(12) United States Patent
Min et al.

(10) Patent No.: US 12,258,618 B2
(45) Date of Patent: Mar. 25, 2025

(54) METHOD FOR CONFIRMING INTRODUCTION OF FOREIGN GENE INTO CELLS AND METHOD FOR MANUFACTURING INTRODUCTION FOREIGN GENE INTO CELLS

(71) Applicant: SEOUL NATIONAL UNIVERSITY R&DB FOUNDATION, Seoul (KR)

(72) Inventors: Dal-Hee Min, Seoul (KR); Yeajee Yim, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 262 days.

(21) Appl. No.: 17/016,691

(22) Filed: Sep. 10, 2020

(65) Prior Publication Data
US 2021/0102241 A1 Apr. 8, 2021

Related U.S. Application Data

(60) Provisional application No. 62/898,039, filed on Sep. 10, 2019.

(30) Foreign Application Priority Data

Sep. 10, 2020 (KR) .......................... 10-2020-0116011

(51) Int. Cl.
| | | |
|---|---|---|
| *C12Q 1/68* | (2018.01) | |
| *C12N 9/22* | (2006.01) | |
| *C12N 15/113* | (2010.01) | |
| *C12Q 1/6823* | (2018.01) | |
| *C12Q 1/6841* | (2018.01) | |
| *C12Q 1/6876* | (2018.01) | |

(52) U.S. Cl.
CPC ............ *C12Q 1/6823* (2013.01); *C12N 9/22* (2013.01); *C12N 15/113* (2013.01); *C12Q 1/6841* (2013.01); *C12Q 1/6876* (2013.01); *C12N 2310/20* (2017.05); *C12Q 2600/178* (2013.01)

(58) Field of Classification Search
CPC .. C12Q 1/6823; C12Q 1/6841; C12Q 1/6876; C12Q 2600/178; C12N 9/22; C12N 15/113; C12N 2310/20
See application file for complete search history.

(56) References Cited

U.S. PATENT DOCUMENTS 10,809,196 B2 * 10/2020 Won .......................... C12N 1/20

FOREIGN PATENT DOCUMENTS

| KR | 10-2011-0007202 A | 1/2011 | |
|---|---|---|---|
| KR | 10-1496671 B1 | 3/2015 | |
| KR | 10-2015-0128612 A | 11/2015 | |
| KR | 10-2016-0063066 A | 6/2016 | |
| KR | 10-2017-0040080 A | 4/2017 | |
| KR | 10-2019-0086259 A | 7/2019 | |
| WO | WO-2017057823 A1 * | 4/2017 | ............ C01B 32/23 |

OTHER PUBLICATIONS

Gemini et al.(2018) A Comparison of Techniques to Evaluate the Effectiveness of Genome Editing, Trends in Biotechnology, vol. 36, No. 2, pp. 147-159. (Year: 2018).*
Dai et al. (2016) Cytoplasmic Drosha activity generated by alternative splicing, Nucleic Acids Research, vol. 44, No. 21, pp. 10454-10466, DOI: 10.1093/har/gkw668 (Year: 2016).*
Li et al. (2015) Outbred genome sequencing and CRISPR/Cas9 gene editing in butterflies, Nature Communications, 6:8212, p. 1-10, DOI: 10.1038 (Year: 2015).*
Gussoni et al; Nature Biotechnology, vol. 14, 1996; pp. 1012-1016 (Year: 1996).*
Seyhan (Mol. BioSyst., 2016, 12, 295-312).*
Office action issued on Apr. 26, 2022 from Korean Patent Office in a counterpart Korean Patent Application No. 10-2020-0116011 (all the cited references are listed in this IDS.) (English translation is also submitted herewith.).
Notice of Allowance issued on Mar. 14, 2023 from Korean Patent Office in a counterpart Korean Patent Application No. 10-2020-0116011 (all the cited references are listed in this IDS.) (English translation is also submitted herewith.).

* cited by examiner

*Primary Examiner* — Jehanne S Sitton
(74) *Attorney, Agent, or Firm* — The PL Law Group, PLLC

(57) ABSTRACT

A method for introducing a foreign gene into a cell according to an embodiment of the present disclosure can easily identify foreign gene introduction by detecting whether there is fluorescent emission or not, and can reduce influence of additional elements other than a target gene since any reporter gene or selectable marker is not required. Further, the inventive method does not need an additional sampling process and therefore may implement a relatively accurate and simple screening process.

20 Claims, 9 Drawing Sheets
Specification includes a Sequence Listing.

a

| Target gene | Clone ID | Knockin/Total |
|---|---|---|
| DROSHA | #9 | 10/10 |
| | #11 | 4/9 |
| | #17 | 5/8 |
| | #20 | 7/9 |
| | #25 | 10/10 |
| DGCR8 | #4 | 6/9 |
| | #23 | 5/8 |
| | #35 | 6/10 |
| | #41 | 2/9 |
| | #43 | 5/9 | b

METHOD FOR CONFIRMING INTRODUCTION OF FOREIGN GENE INTO CELLS AND METHOD FOR MANUFACTURING INTRODUCTION FOREIGN GENE INTO CELLS

CROSS REFERENCE TO RELATED APPLICATIONS AND CLAIM OF PRIORITY

This application claims the benefit of U.S. Provisional Patent Application No. 62/898,039 filed on Sep. 10, 2019 and the benefit of Korean Patent Application No. 10-2020-0116011, filed on Sep. 10, 2020, the disclosures of which are incorporated herein by reference for all purposes.

FIELD OF THE INVENTION

The present invention relates to a method for identifying introduction of foreign genes into cells and a method for production of foreign gene-introduced cells.

DESCRIPTION OF THE RELATED ART

Genome engineering technique using CRISPR-Cas9 enables faster and more convenient knockout and knock-in of specific gene in a desired site, and is currently and actively used in a number of biological studies. However, a technique for screening positive cells or targeted cells successfully gene-edited by CRISPR-Cas9 still depends on a classical way that uses selectable markers such as reporter gene, antibiotic-resistant gene, etc. These methods should introduce additional elements in addition to a target gene, which may influence on target gene expression or the structure and function of a protein, hence entailing limitation.

Another standard technique is to use quantitative polymerase chain reaction (PCR) and DNA sequencing. However, these methods need human labor and costs to manage a number of samples, and thus are not suitable for mass screening.

Accordingly, establishment of an enrichment strategy to rapidly and selectively enrich only cells completely gene-edited without using the reporter gene or selectable marker is urgently required.

SUMMARY

An object of the present invention is to provide a method for easily identifying whether foreign gene is introduced into a target cell or not.

Another object of the present invention is to provide a method capable of easily selecting foreign gene-introduced cells to produce the foreign gene-introduced cells.

To achieve the above objects, the following technical solutions are adopted in the present invention.

1. A method for identifying introduction of foreign gene into a cell, the method including: introducing foreign genes into target cells; treating the foreign gene-introduced cells with a graphene oxide sensor in which a water-soluble polymer and a fluorescent conjugated probe are bound to a surface thereof; and detecting fluorescent emission in the cells, wherein the probe is specifically bound to a material produced in the target cells by introduction of the foreign genes.
2. The method according to the above 1, wherein the foreign gene introduction is performed by transformation, transfection, transduction, gene transfer, conjugation or gene scissors.
3. The method according to the above 1, wherein the foreign gene introduction is performed using CRISPR-Cas9.
4. The method according to the above 1, wherein the water-soluble polymer is any one selected from the group consisting of chitosan, chitosan salts, dextran, hyaluronic acid, hyaluronic acid salts, pectin, pectin salts, alginate, alginic acid, agar, galactomannan, galactomannan salts, xanthan, xanthan salts, polyethyleneglycol (PEG), polyethyleneimine (PEI), and a combination thereof.
5. The method according to the above 1, wherein the graphene oxide is graphene oxide nanocolloids.
6. The method according to the above 1, wherein the probe is any one selected from the group consisting of antibody, nucleic acid, peptide, protein and a combination thereof.
7. The method according to the above 1, wherein the material is mRNA or miRNA, and the probe is PNA specifically bound to the material.
8. A method for production of foreign gene-introduced cell, including: introducing foreign genes into target cells; treating the foreign gene-introduced cells with a graphene oxide sensor in which a water-soluble polymer is bound to a carboxyl group portion of a surface thereof and a fluorescent conjugated probe is bound to the remaining portion of the surface to which the water-soluble polymer is not bound; detecting fluorescent emission in the cells; and incubating cells in which emission is detected, wherein the probe is specifically bound to a material produced in the target cells by introduction of the foreign genes.
9. The method according to the above 8, wherein the water-soluble polymer is any one selected from the group consisting of chitosan, chitosan salts, dextran, hyaluronic acid, hyaluronic acid salts, pectin, pectin salts, alginate, alginic acid, agar, galactomannan, galactomannan salts, xanthan, xanthan salts, polyethyleneglycol (PEG), polyethyleneimine (PEI), and a combination thereof.
10. The method according to the above 8, wherein the graphene oxide is graphene oxide nanocolloids.

Conventionally, in order to screen cells with completed gene introduction, a selectable marker such as a reporter gene or an antibiotic-resistant gene has been used. The conventional method needs to introduce additional elements as well as a target gene, and therefore, entails limitation since such additional elements may influence on target gene expression or the structure and function of a protein.

On the other hand, the method according to the present invention has advantage of overcoming limitation of the existing methods since cells having completed gene introduction can be selected by detection of fluorescent emission without using the reporter gene or selectable marker.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION

Figure 1:
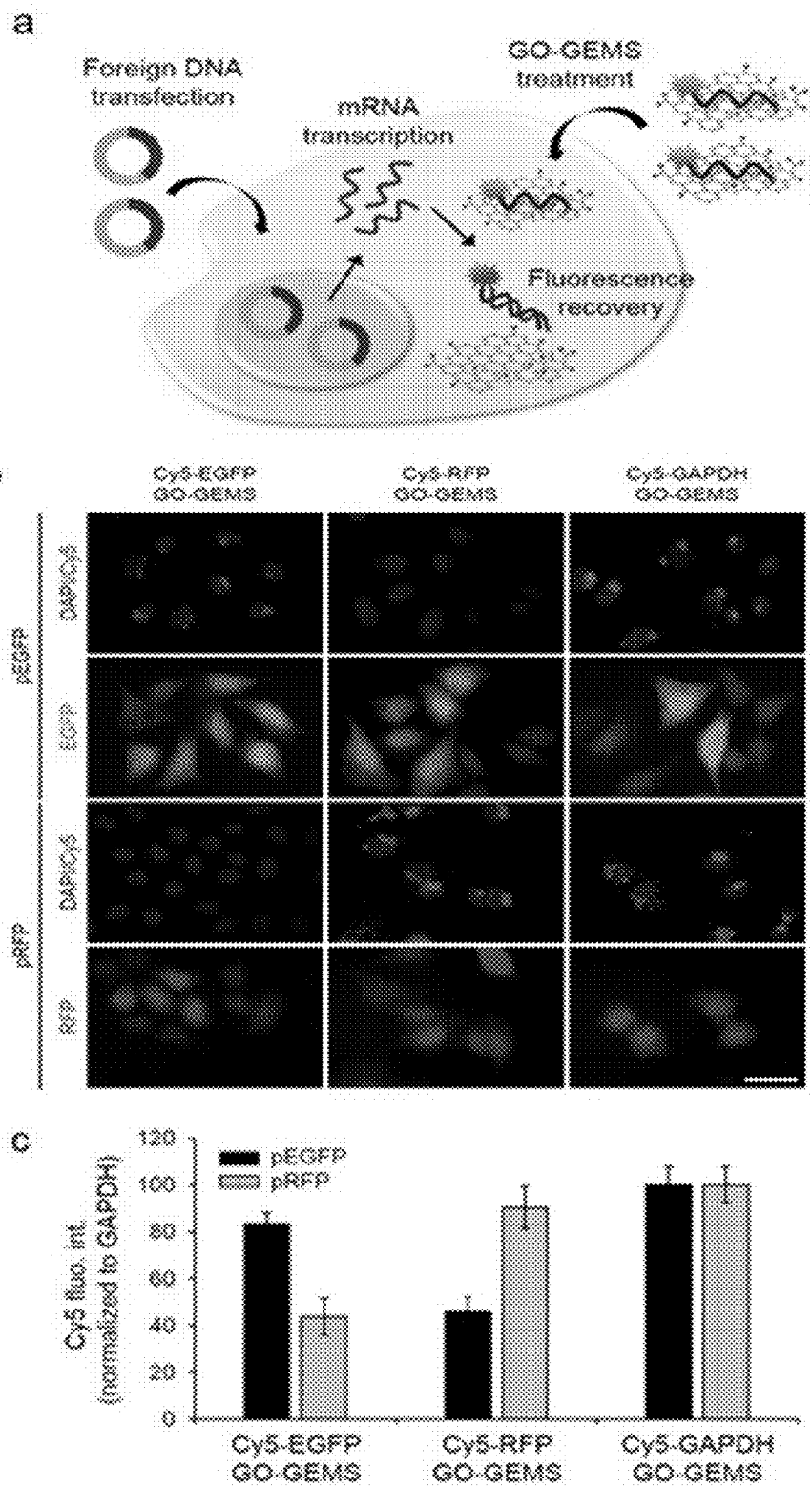
FIG. 1 is diagrams illustrating results of quantitative and qualitative analyses of EGFP and RFP mRNA in regard to HeLa cell transduced with pEGFP or pRFP plasmid, and demonstrating that quantitative and qualitative analyses of specific mRNA in the cells are possible using the inventive sensor.

Hereinafter, the present invention will be described in detail.

The present invention provides a method for identifying introduction of foreign gene into a cell, which includes: introducing foreign genes into target cells; treating the foreign gene-introduced cells with a graphene oxide sensor in which a water-soluble polymer is bound to a carboxyl group portion of a surface thereof and a fluorescent conjugated probe is bound to the remaining portion of the surface to which the water-soluble polymer is not bound; and detecting fluorescent emission in the cells, wherein the probe is specifically bound to a material generated in the target cell by introduction of the foreign gene.

First, a foreign gene is introduced into a target cell.

The target cell is a cell into which the foreign gene is introduced, and such a foreign gene may be transduced by a variety of methods known in the art. Therefore, types of the target cells are not particularly limited but may include any cell so long as it can generate specific materials by introduction of the foreign gene. For example, the target cell may be diverse cells such as cells of human, animals other than human, plants, microorganisms, etc. According to one embodiment of the present invention, human uterine cervical cancer cells, human embryonic renal cells, etc. have been used, but it is not limited thereto.

The foreign gene may include all genes other than genes present in the target cell. All genes may be used without limitation thereof so long as they allow the target cell to generate specific materials by introduction. According to one embodiment of the present invention, the foreign gene may be a gene possibly inserted in DROSHA or DGCR8 gene site (DiGeorge syndrome critical region gene 8) by applying CRISPR-Cas9-mediated gene knock-in technique, more particularly, a gene possibly tag-inserted at C-terminal of DROSHA or a gene possibly tag-inserted at N-terminal of DGCR8, and for example, 3×FLAG-2×Strep tag gene, but it is not limited thereto.

Introduction of the foreign gene into the target cell may be performed by all genetic engineering processes known in the art, and more particularly, transformation, transfection, transduction using phages or viruses, gene transfer to artificially introduce a foreign gene, or a process for introducing a gene into a host that is easy for gene transfer or introduction, followed by conjugation, and the like, may be used.

For transformation or transfection, various carriers may be used. For example, viral vectors, plasmids, naked DNA, liposome, tRNA, bacterial vectors, cationic lipid transducer, cationic polymer transducer, silica nanoparticles, carbon nanomaterials, gold nanoparticles, porous nanoparticles, and the like, may be used.

For transduction, various bacteriophages or viruses may be used. For example, adenovirus, adeno-associated virus (AAV), retro-virus, herpes virus, herpes simplex virus, vaccinia virus, lentivirus, or fox virus, and the like, may be used.

Gene transfer may be performed by, for example, use of genetic scissors, calcium phosphate precipitation using host cells, calcium chloride treatment, protoplast fusion, sonoporation, electroporation, polynucleotide encapsulation in liposomes, microinjection, RBC ghost fusion, or lipofection using liposome and the like.

The genetic scissors may include, for example, use of CRISPR, and more particularly, use of CRISPR-Cas9, but it is not limited thereto.

Next, the surface of foreign gene-introduced cell is treated with a graphene oxide sensor in which a water-soluble polymer and a fluorescent conjugated probe are bound to a surface thereof.

In the graphene oxide sensor, the water-soluble polymer is bound to a portion of the surface of graphene oxide and the fluorescent conjugated probe is bound to the remaining portion of the surface of graphene oxide.

Graphene oxide may be in a form of particles or sheet.

Graphene oxide has a particle diameter of, for example, about 10 to 500 nm, about 10 to 200 nm, about 10 to 150 nm, about 10 to 100 nm, about 10 to 50 nm, about 20 to 200 nm, about 20 to 150 nm, about 20 to 100 nm, about 20 to 50 nm, about 30 to 200 nm, about 30 to 150 nm, about 30 to 100 nm, about 30 to 50 nm, about 50 to 200 nm, about 50 to 150 nm, about 50 to 100 nm, about 50 to 80 nm, about 60 to 200 nm, about 60 to 100 nm, about 60 to 80 nm, about 80 to 200 nm, about 80 to 150 nm, about 80 to 100 nm, about 90 to 200 nm, about 90 to 150 nm, or about 90 to 100 nm, but it is not limited thereto. According to one embodiment of the present invention, the graphene oxide particle may have a particle diameter of 50 to 80 nm, 90 to 200 nm, 90 to 150 nm, or 80 to 100 nm. Herein, the particle diameter is a value calculated by averaging experimental values measured using dynamic light scattering or sizes shown in atomic force microscopy (AFM) or transmission electron microscopy (TEM) images, and means a value obtained, provided if graphene oxide has a spherical or circular shape.

Graphene oxide may be selected from the group consisting of nanographene oxide (NGO) and a derivative thereof, reduced graphene oxide and a derivative thereof, graphene oxide nanocolloids (GON), and a combination thereof, and more particularly, graphene oxide nanocolloids, but it is not limited thereto. Unlike typical graphene oxide prepared from graphite powders, graphene oxide nanocolloids are prepared from graphite nanofibers and distinguished from the graphene oxide in terms of size distribution, edge-to-area ratios and charge density. In aspects of use and sensing ability, graphene oxide nanocolloids are more preferable than the graphene oxide.

The term "water-soluble polymer" as used herein refers to resin or polymer which is soluble in water or dispersible in the form of microparticles in water. The water-soluble polymer may include natural polymer, semi-synthetic polymer or synthetic polymer. The water-soluble polymer possibly used in the present invention may have a molecular weight of 1 to 20 kDa, 5 to 15 kDa or 8 to 12 kDa. According to one embodiment, the water-soluble polymer may have a molecular weight of 10 kDa.

Further, the water-soluble polymer may be selected from the group consisting of chitosan and a derivative thereof, chitosan salts, dextran and a derivative thereof, hyaluronic acid and a derivative thereof, hyaluronic acid salts, pectin and a derivative thereof, pectin salts, alginate and a derivative thereof, alginic acid, agar, galactomannan and a derivative thereof, galactomannan salts, xanthan and a derivative thereof, xanthan salts, beta-cyclodextrin and a derivative thereof, beta-cyclodextrin salts, polyethyleneglycol (PEG), polyethyleneimine (PEI), and a combination thereof. Specifically, the water-soluble polymer may be selected from the group consisting of dextran, polyethyleneglycol, polyethyleneimine and a combination thereof. More specifically, dextran may be used.

The water-soluble polymer may be bound to, for example, a carboxyl group portion of graphene oxide, and particularly, through covalent bond, ionic bond or hydrogen bond, but it is not limited thereto.

The term "probe" as used herein refers to a material specifically bonded to a target material (a material produced in the target cell by foreign gene introduction).

The target material may be a material produced in the target cell by foreign gene introduction, and may include, for example, protein, nucleic acid, hormone, hormone-like substances, enzyme, enzyme inhibitor, signal transduction protein, antibody, monoclonal antibody, binder protein, binder domain, peptide, antigen, metabolic materials, membrane protein, receptor protein, adherence protein, structural protein, regulatory protein, toxin protein, growth factor, cytokine, transcription factor, coagulation factor or plant bio-based resistance inducer protein and the like. Particular examples thereof may include mRNA or miRNA, but it is not limited thereto.

The probe may be bound to the target material as illustrated above, and may include, for example, any one selected from the group consisting of antibody, nucleic acid, peptide, protein and a combination thereof, but it is not limited thereto.

Additionally, all materials known to have high affinity to desired target materials may also be used. According to one embodiment, the antibody may be specifically bound to the epitope of a target protein to allow detection of the target material. Further, if the nucleic acid has a complementary sequence to a nucleic acid sequence of the target material, the nucleic acid may be bound with a target DNA sequence to allow detection of the target material. Further, the peptide may be specifically bound to a receptor or ligand expressed on the surface of the cell to allow detection of the target material.

The nucleic acid may include any one selected from the group consisting of DNA, RNA, mRNA, miRNA, non-translated RNA, double-helix RNA, double-helix DNA, DNA-based enzyme, deoxyribozyme, aptamer, peptide nucleic acid (PNA), locked nucleic Acid (LNA), and a combination thereof. Specifically, PNA may be used.

When the probe is PNA, an amide backbone with neutral charge is included to reduce electrostatic repulsion between other nucleic acids or graphene oxides, thereby attaining stronger interaction. Further, graphene oxide is a substance having different functional groups containing oxygen as well as a graphene structure composed of carbon hexagonal rings, simultaneously, such that the graphene oxide is preferably dispersible in water while maintaining properties of graphene.

Herein, the nucleic acid may consist of 10 to 50, 10 to 30, 12 to 28, 15 to 25, 18 to 22 or 19 to 21 bases. However, if the nucleic acid can form a complementary bond together with the target nucleic sequence, the number of bases is not limited to the above range. According to one embodiment, the nucleic acid may consist of 18 to 22 bases. When the probe consists of 17 or less bases, many repeat sequences exist within a genome sequence and may reduce target-specificity. If the probe consists of 23 or more bases, it may cause deterioration in nucleic acid synthesis yield while increasing costs of synthesis. Further, the nucleic acid is easily self-coagulated due to the increased affinity between probes. Further, affinity between probe and the target material is also increased to cause a problem of increasing possibility for binding the target material on the probe even if the target material is not absolutely complementary to the probe.

According to the present invention, the fluorescent conjugated probe means that a fluorescent material is bound to the probe. The fluorescent material absorbs fluorescent energy by graphene oxide bound with the water-soluble polymer and is present in a quenching state. When the probe is specifically bound to the target material and is free from graphene oxide, the fluorescent material becomes fluorescent. The fluorescent material may be bound to one end or in a middle of the probe. When the probe is nucleic acid, the fluorescent material may be present at 5'- or 3'-position or inside the nucleic acid. If the probe is peptide, the fluorescent material may be bound to N-terminal, C-terminal or inside the peptide. The fluorescent material may be bound with the probe directly or through a crosslinker.

The fluorescent material may include, for example, any one selected from the group consisting of fluorescein, fluorescein chlorotriazinyl, rhodamine green, rhodamine red, tetramethyl rhodamine, fluorescein isothiocyanate (FITC), Oregon green, alexfluoro, carboxyfluorescein (FAM), 6-carboxy-4',5'-dichloro-2',7'-dimethoxyfluorescein (JOE), carboxy-X-rhodamine (ROX), 6-carboxy-2',4,4',5',7,7'-hexachlorofluorescein (HEX), Texas red (sulforhodamine 101 acid chloride), 6-carboxy-2',4,7',7-tetrachlorofluorescein (TET), tetramethylrhodamine-isothiocyanate (TRITC), carboxytetramethyl rhodamine (TAMPA), cyanine-based dyes, ciadi carbocyanine dyes, and a combination thereof. The cyanine-based dyes may be selected from the group consisting of Cy3, Cy5, Cy5.5, Cy7 and a combination thereof.

Further, fluorescent emission in the cell is detected or identified.

The foreign gene-introduced target cell generates a target material by introduction of the foreign gene. Then, a fluorescent conjugated probe is released from the graphene oxide sensor, thereby detecting fluorescent emission in the cells. Therefore, the cell having detected fluorescent emission may be determined as the foreign gene-introduced cell.

Fluorescence may be detected by determining that a fluorescent material quenched by graphene oxide emits light while being isolated from a target material when the fluorescent material specifically contacts or bonds to the target material. In order to measure a level of fluorescence, flow cytometry, fluorescence activated cell sorting (FACS) or analysis of fluorescent signals or images may be used, but it is not limited thereto.

The present invention provides a method for production of foreign gene-introduced cell, which includes: introducing foreign genes into target cells; treating a surface of the foreign gene-introduced cells with a graphene oxide sensor in which a water-soluble polymer is bound to a carboxyl group portion of a surface thereof and a fluorescent conjugated probe is bound to the remaining portion of the surface to which the water-soluble polymer is not bound; detecting fluorescent emission in the cells; and incubating cells in which emission is detected, wherein the probe is specifically bound to a material generated in the target cell by introduction of the foreign gene.

The respective steps of the above production method are the same as described above.

Materials produced by the probe and the target cell are the same as described above.

A method for production of foreign gene-introduced cells according to the present invention may further include incubating cells in which emission is detected, which is different from the above method for identifying whether the foreign gene is introduced or not.

As described above, since the cells in which emission is detected are foreign gene-introduced cells, it is possible to obtain the foreign gene-introduced cell by incubating the cells.

If necessary, in order to more completely isolate the foreign gene-introduced cells only, the method may further include sorting only the cells in which emission is detected.

For example, the sorting step may be performed by flow cytometry, fluorescence activated cell sorting (FACS), magnetic activated cell sorting (MACS), laser capture microexcision or DEP array sorting, and the like, but it is not limited thereto.

Hereinafter, the present invention will be described in more detail by means of examples.

Preparative Example

1. Preparation of Graphene Oxide Nanocolloids (GON)
    (1) After putting 50 mL of $H_2SO_4$ in a round-bottom flask, 4 g of $K_2S_2O_8$ and 4 g of $P_2O_5$ were fed and agitated to completely dissolve the same. Then, 2 g of graphite nanofiber was added and heated at a temperature of 90 to 100° C. under agitation for 15 to 24 hours. The mixture was cooled to room temperature, followed by slowly adding 250 mL of distilled water to dilute the mixture.
    (2) The diluted mixture was filtered using a filter paper and the reagent residue was sufficiently washed out using 1000 mL of distilled water, followed by drying under vacuum.
    (3) After placing the round-bottom flask in an ice bath, 250 mL of $H_2SO_4$ was added and the pre-oxidized graphite nanofiber prepared in the following section (4) (about 1.5 g) was further added thereto. This mixture was agitated while slowly adding 10 g of $KMnO_4$. After about 6 hours, 1000 mL of distilled water was slowly added to the reactant to dilute the same while placing the flask in the ice bath. Then, 50 mL of 30% $H_2O_2$ aqueous solution was slowly added, the mixture was washed with 3.4% HCl aqueous solution three times (with centrifugation at 1200 rpm for 30 minutes each time), and then washed again with acetone three times. Then, acetone was removed by evaporating brown acetone supernatant under vacuum.
    (4) The obtained solid product was homogeneously dispersed in distilled water, followed by dialysis using a 10,000 Da membrane tube until the solution becomes neutral. The purified solution was lyophilized to prepare GON powders. 50 mg of GON was put in 50 mL of 0.1% dextran aqueous solution and subjected to ultra-sonication for 30 minutes. Thereafter, 25 µL of 25% ammonia aqueous solution was added to the treated mixture after heating the same at 95° C., followed by heating the resulting solution for 3 hours under agitation.
    (5) After purification with repeated centrifugation, the product was subjected to dialysis using 10,000 Da membrane tube until the solution becomes neutral.

2. Preparation of Graphene Oxide Nanocolloids (DReGON) Coated with Dextran

The surface of graphene oxide nanocolloids obtained in Example 1 above was coated using dextran. Specifically, 50 mg of graphene oxide nanocolloids was dispersed in 50 ml of distilled water, followed by adding 0.1% (w/w) dextran aqueous solution thereto. After ultra-sonication of the mixture for 30 minutes, 25 µl of ammonia aqueous solution was added and allowed to react at 95° C. under agitation for 3 hours. After washing the reaction product with distilled water, the solution was subjected to centrifugation for 30 minutes under a condition of 10,000 rpm, and lyophilized to produce a final product, that is, DReGON.

AFM image of the produced DReGON was obtained using NTEGRA spectra (NT-MDT, Russia) (a of FIG. 3), and was analyzed in line profile using NOVA software provided along with the relevant device. From the above image, it could be confirmed that the DReGON produced with a thickness of 3 to 6 nm and a size of 20 to 60 nm was synthesized. UV-Visible absorption spectrum was obtained by UV-Vis spectrometer S-3100 (Scinco, Korea) with a maximum absorbance peak appeared at 226 nm, which corresponds to $\pi$-$\pi$*transition of aromatic C=C bond (b of FIG. 3).

Figure 3:
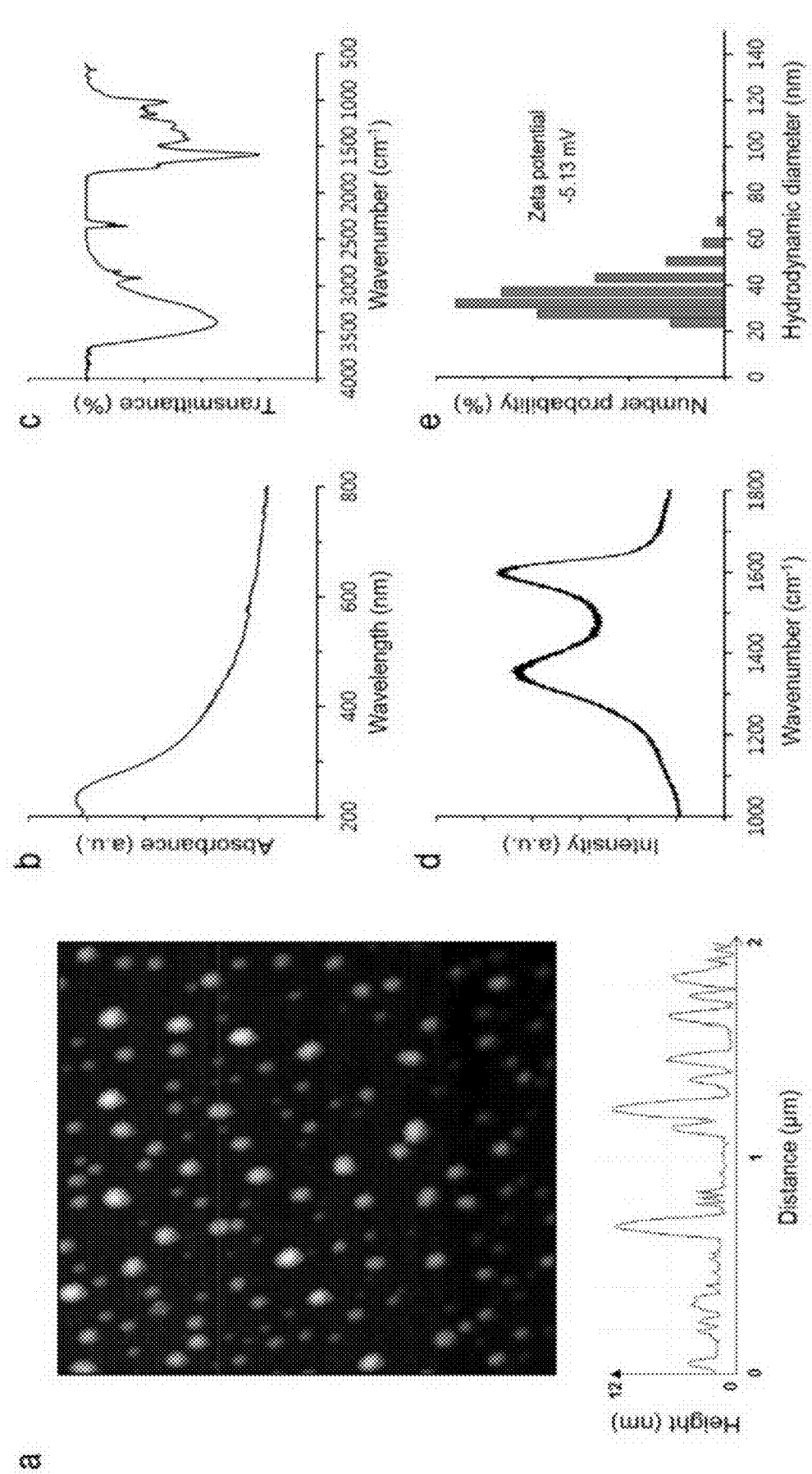
FIG. 3 is diagrams illustrating characteristics of graphene oxide nanocolloids, wherein a of FIG. 3 illustrates an atomic force microscopy (AFM) image, b of FIG. 3 illustrates UV-Visible ray absorption spectrum, c of FIG. 3 illustrates FT-IR (Fourier transform infrared) spectrum, d of FIG. 3 illustrates Raman spectrum, and e of FIG. 3 illustrates dynamic light scattering (DLS) data.

Raman spectra were measured by LabRAM HR UV-vis-NIR (Horiba Jobin Yvon, France) using CW laser (514.5 nm) as an excitation source centralized through an objective lens (50×, numerical aperture NA=0.5) as well as a BXFM confocal microscope (d of FIG. 3). FT-IR spectrum was measured by Vertex 70 FT-IR spectrometer equipped with HYPERION 100 microscope (Bruker, USA) (c of FIG. 3), while DLS and Z potential measurement was implemented by Zetasizer NanoS (Malver Instruments, United Kingdom) (e of FIG. 3).

c of FIG. 3 illustrates that the produced DReGON has different oxygen-containing functional groups, while d of FIG. 3 illustrates specific peaks at 1355 $cm^{-1}$ in a dissipative graphite structure and at 1599 $cm^{-1}$ in an aligned graphite structure, respectively, wherein it was confirmed that D/G peak intensity ratio ($I_D/I_G$) was about 0.94. Referring to e of FIG. 3, a mean hydrodynamic radius was about 35 nm and Z potential was −5.13 mV.

3. Preparation of GO-GEMS Complex (Graphene Oxide-Based Gene Expression Monitoring Sensor)

GO-GEMS complex was prepared by adding graphene oxide nanocolloids coated with dextran, which was produced in Example 2 above, to Cy5 (Cyanine 5, ex/em=640/

670)-labeled PNA solution. As a result of mixing 1.2 μg of graphene oxide nanocolloids and 20 pmol of 1 Cy5-PNA probe in 50 μL of phosphate buffer saline (PBS), 95% or more of Cy5 fluorescence was quenched and used for cell-based experiments. In a case of 3×FLag-2×Strep tag, a total 20 pmol of Cy5-PNA mixture containing 3 types of PNA probes in the same amount was used to improve screening performance.

Example

1. Cell Culture

Human uterine cervical cancer cell line, that is, HeLa cell was incubated in DMEM (Dulbecco's Modified Eagle's medium) containing 4.5 g/L D-glucose, and supplemented with 10% FBS (fetal bovine serum), 100 units/mL of penicillin, 100 units/mL of streptomycin, etc. Human embryonic renal cell 293 EBNA1, that is, HEK293E cell was incubated in DMEM containing 4.5 g/L D-glucose, and supplemented with 5% FBS, 100 units/mL of penicillin, 100 units/mL of streptomycin and 50 μg/mL of G418. The cells were maintained in a humid $CO_2$ incubator (37° C., $CO_2$ 5%).

2. Transduction

HeLa and HEK293E cells were incubated in 6-well culture plate for 18 hours. 1 μg of plasmid and 2.5 μL of Lipofectamine 2000 (Invitrogen; Thermo Fisher Scientific Inc., USA) were mixed with 100 μL of non-serum medium, and then added to cells in 900 μL of complete medium according to instructions of the manufacturer. The transduced cells were taken and moved for further experiments 1 day after culture.

3. Interpretation of Intracellular Fluorescence by GO-GEMS (1) First, two types of plasmids that encode green fluorescent protein (EGFP) and red fluorescent protein (RFP), respectively, were used to detect mRNA transcripted in plasmid DNA (a of FIG. 1).

After transduction, HeLa cells were moved to a 96-well culture plate and, after 12 hours, treated with Cy5-labeled GO-GEMS complex in a non-serum medium. Following 14 hour culture, intracellular fluorescence analysis was performed. Fluorescent image of the cells was obtained by Ti inverted fluorescence microscope equipped with 40× objective lens (Olympus IX 71, Japan), as well as CoolSNAPcf charged-bound device (CCD) camera (Photomatrix, USA) including Metamorph image assay software (Molecular Devices, USA). Intracellular fluorescence was measured using a flow cytometry system, that is, FACSCanto II (BD Bioscience, USA), and fluorescent images for quantitative analysis were obtained by an automatic cell imaging system, that is, In Cell analyzer 2000 (GE Healthcare, United Kingdom), wherein the analysis was performed using a multi-target analysis module software in In Cell analyzer 1000 Workstation.

After pEGFP or pRFP transduction, human uterine cervical cancer cell line, that is, HeLa cells cultured along with Cy5 (Cyanine5)-labeled EGFP or RFP GO-GEMS exhibited fluorescence corresponding to transduced plasmid without cross-reaction (b of FIG. 1). In b of FIG. 1, a scale bar was 50 μm.

(2) In order to identify target mRNA-specific fluorescent emission based on housekeeping gene expression, a fluorescent PNA probe complementary to GAPDH (glyceraldehyde-3-phosphate dehydrogenase) mRNA was used to detect fluorescent emission. Sequence information of all PNA probes used in the experiments is listed in Table 1 below. Using an automatic cell imaging system, that is, In-Cell analyzer, fluorescent signals were quantified (c of FIG. 1).

As a result, for HeLa cell introduced with green fluorescent protein (EGFP) plasmid, fluorescence of PNA probe complementary to EGFP mRNA was higher than fluorescence of PNA probe complementary to RFP mRNA. On the contrary, for HeLa cell introduced with red fluorescent protein (RFP) plasmid, fluorescence of PNA probe complementary to RFP mRNA was higher than fluorescence of PNA probe complementary to EGFP mRNA. Further, it was demonstrated that GO-GEMS complex using fluorescent PNA probe complementary to GAPDH mRNA showed substantially constant fluorescent signals, regardless of types of introduced plasmids. Further, GO-GEMS having a scrambled sequence showed almost no fluorescent signal.

Consequently, it could be seen that GO-GEMS is an excellent sensor specifically responding to target mRNA and generates very little noise signals.

TABLE 1

| SEQ IN NO: | Target | Sequence of PNA probe |
|---|---|---|
| 1 | GAPDH | GAGTCCTTCCACGATACCA |
| 2 | EGFP | AAGTCGTGCTGCTTCATGT |
| 3 | RFP | TTCTTGGATCTGTATGTGG |
| 4 | 3xFLAG-2xStrep tag | GTGGCTCCAAGCAGATCCT |
| 5 | | CGCCCTTCTCAAACTGAGG |
| 6 | | TGTAGTCGATGTCGTGATC |
| 7 | scrambled | ATCGAATAGTCTGACTACAACT |

As a result, it could be seen that the transduced HeLa cell was cultured along with Cy5-scrambled GO-GEMS complex and did not have significant fluorescence recovery, however, showed high level of fluorescent emission by treatment using Cy5-GAPDH GO-GEMS. An increase in fluorescent emission is substantially coincident with existing quantitative analysis using flow cytometry (FIG. 4), which demonstrates that the GO-GEM based mRNA detection system is excellent in sequence-specific detection of mRNA expression after plasmid transduction.

Figure 4:
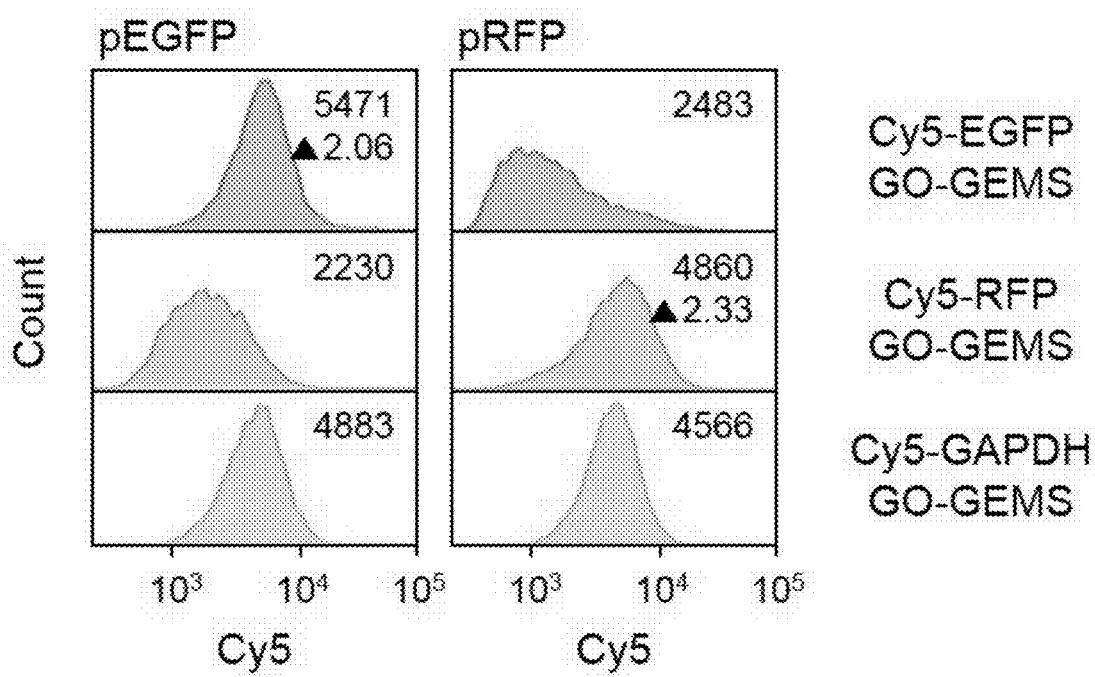
FIG. 4 is diagrams illustrating flow cytometry data to EGFP or RFP mRNA signals in HeLa cell transduced with pEGFP or pRFP plasmid.

Specifically, FIG. 4 is graphs illustrating the number of cells having fluorescent emission under separate conditions, which are similar to aspects and results of the graphs in c of FIG. 1.

4. Identification of Superiority of GO-GEMS Composite by Determination of Z' Factor Cy5-GAPDH and Cy5-scrambled GO-GEMS complexes were prepared in PBS. Each sensor complex was added to HEK293E cell for 14 hours, and fluorescent signals were analyzed by means of In Cell analyzer 2000 together with In Cell 1000 Workstation software (n=30). Z' factor is used to assess suitability of a system with regard to high capacity screening, and generally used to evaluate the quality of an analysis system.

Figure 5:
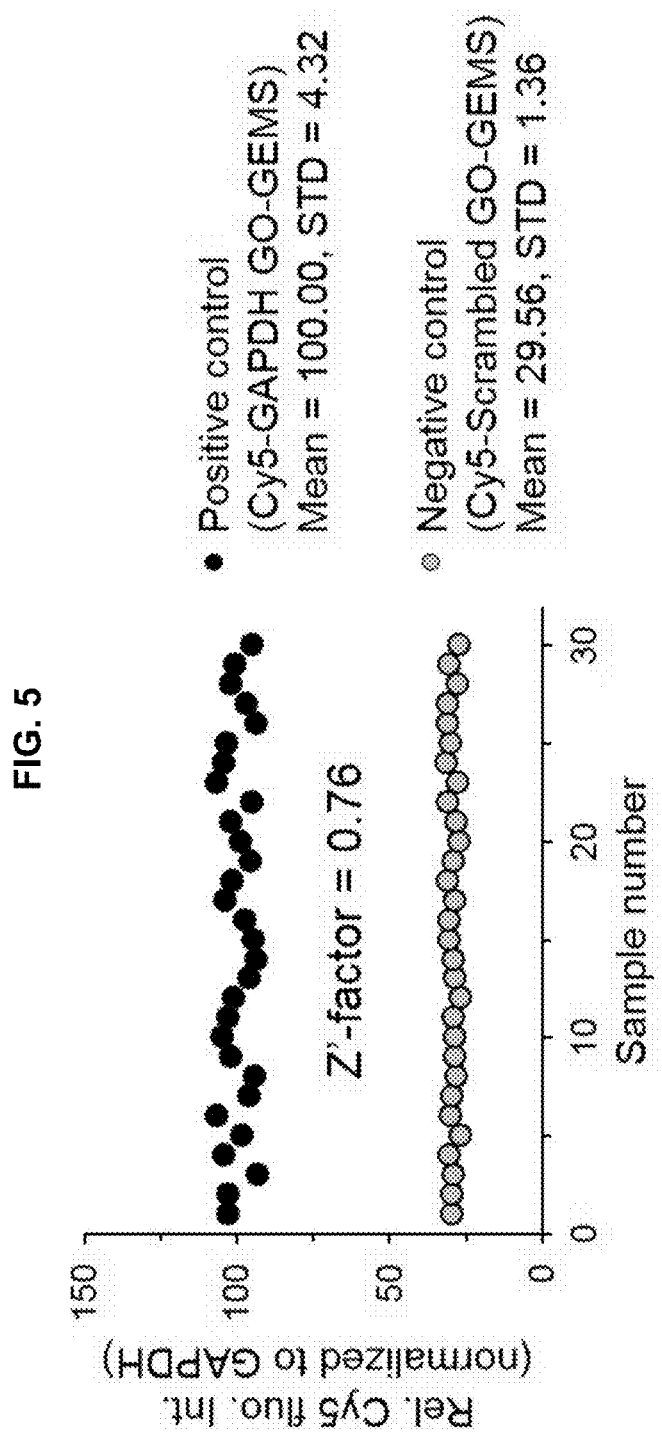
FIG. 5 is a diagram illustrating results of calculating Z' factor of GO-GEMS complex.

Z' factor was calculated by applying the following Mathematical Equation 1 and results thereof are illustrated by graphs in FIG. 5. Four (4) parameters refer to mean values (μ) and standard errors (σ) of positive control (c+), negative control (c−), respectively.

$$Z'\text{-factor} = 1 - \frac{(3\sigma_{c+} + 3\sigma_{c-})}{|\mu_{c+} - \mu_{c-}|} \quad \text{[Mathematical Equation 1]}$$

As a result, in a case of 30 positive controls (GAPDH) and 30 negative controls (scrambled), Z' factor was 0.76. In general, if Z' factor is larger than 0.5, this is recognized as an assay method suitable for mass-screening. Therefore, GO-GEMS system described above may be determined to be suitable for high capacity screening.

5. Preparation of Gene Knock-in Cell Using CRISPR/Cas9

After determining Z' factor, a target gene in actual application was searched in order to screen Z' tag knock-in. In the gene engineering, most of target genes have considerably lower expression level than that of housekeeping gene such as GAPDH or actin. Therefore, it is important to detect mRNA having a low expression level so as to improve platform applicability. Accordingly, in order to select DROSHA gene (SEQ ID NO: 8) and DGCR8 gene (SEQ ID NO: 9) which express essential elements required for microRNA as CRISPR-Cas9-mediated tag knock-in target, and in order to conduct efficient screening for sorting tag knock-in cells, fluorescent emission of mRNA transcripted from the gene was detected.

3×FLAG-2×Strep tag (SEQ ID NO: 10) used in the examples of the present invention is one of protein tags widely used in the art in order to implement highly effective and specific sorting of protein complexes.

Figure 2:
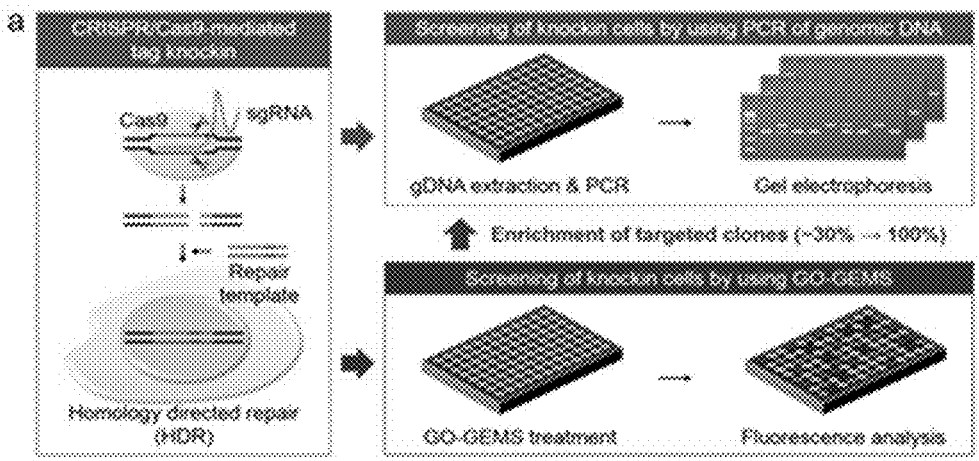
FIG. 2 is diagrams illustrating screening of 3×FLAG-2× Strep tagged mRNA in HEK293E monocyte-derived clone after gene introduction using CRISPR-Cas9, which demonstrate that tagged mRNA could be detected.
Figure 2:
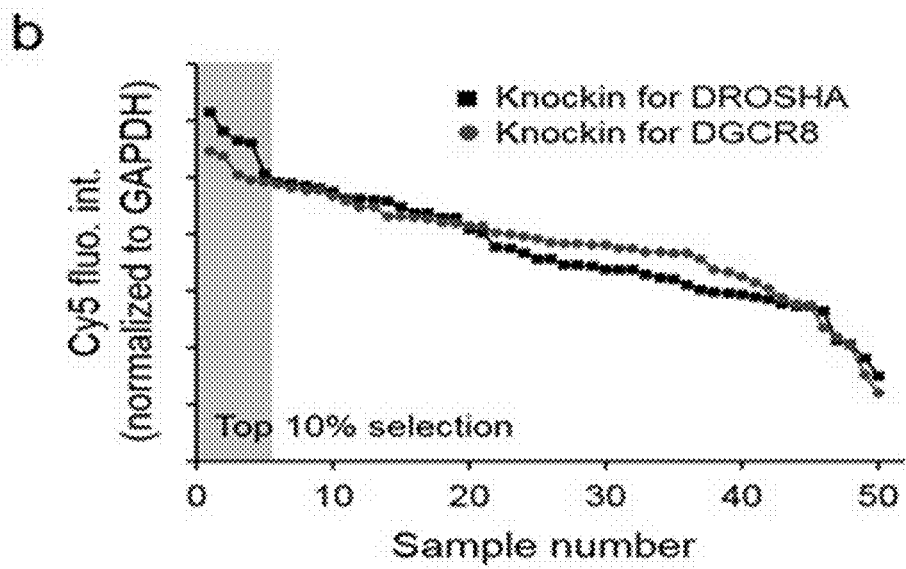
Figure 2:
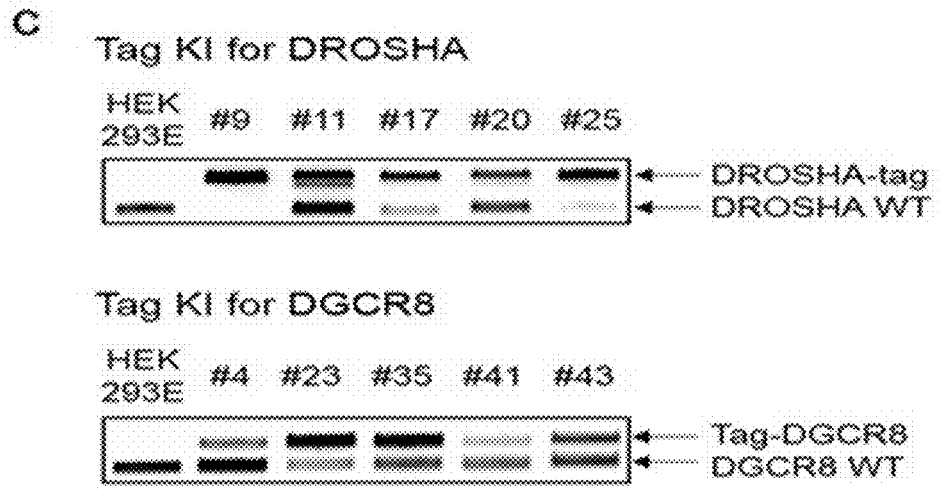
Figure 6:
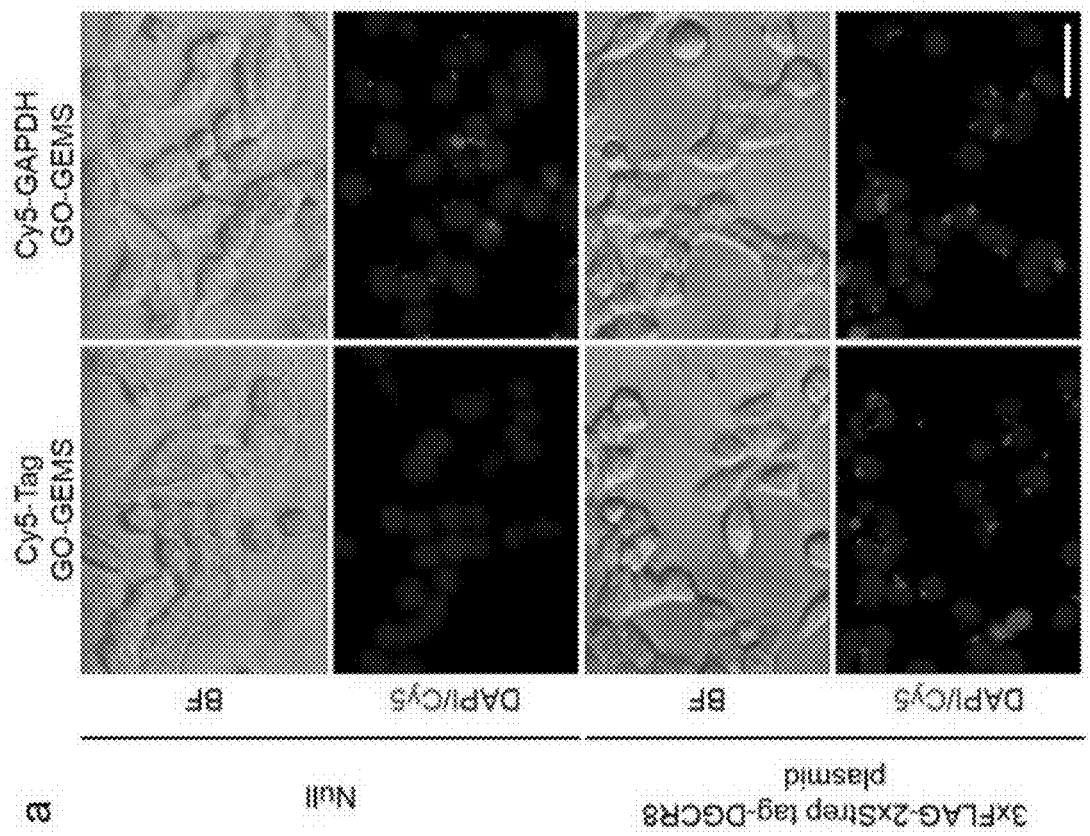
FIG. 6 is diagrams illustrating qualitative and quantitative analysis results of tag mRNA in HEK293E cells transduced with 3×FLAG-2×Strep-DGCR8 plasmid.

In order to produce 3×FLAG-2×Strep knock-in cell-line, CRISPR guide sequences were designed to target C-terminal of human DROSHA coding region or N-terminal of human DGCR8 coding region, respectively. Specifically, sgRNA was designed using CRISPR DESIGN TOOL provided by Feng Zhang group. a of FIG. 2 illustrates a specific schematic view thereof. Before screening, tag-specific GO-GEMS system was identified in the temporarily transduced cell using a plasmid encoding 3×FLAG-2×Strep-DGCR8 fusion protein. After transduction of fused gene, HEK293E cell cultured along with Cy5-tagged GO-GEMS complex exhibited Cy5 fluorescent signal occurred by hybridization of PNA probe and tag mRNA (FIG. 6). As a result, it could be seen that the transduced cell exhibited higher fluorescence than non-introduced cell (Null). When 3×FLAG-2×Strep tag knock-in in DGCR8 was progressed, mRNA sequence of 3×FLAG-2×Strep-DGCR8 fusion protein has a specific sequence (SEQ ID NO: 11). Further, a coding region at which the fusion protein is expressed has a specific sequence (SEQ ID NO: 12), while a fresh sequence inserted into DGCR8 gene has a specific sequence (SEQ ID NO: 13).

Double-stranded oligo encoding sgRNA sequence (SEQ ID NOS: 14 to 17) was linked to BbsI-digested pX458 plasmid (Feng Zhang; Addgene #48138) including SpCas9 coding sequence (SEQ ID NO: 18). Specifically, DROSHA_sgRNA-upper sequence corresponds to caccgTAAAGGAGGGCATGCAAGTG (SEQ ID NO: 14), DROSHA_sgRNA-lower sequence corresponds to aaacCACTTGCATGCCCTCCTTTAc (SEQ ID NO: 15), DGCR8_sgRNA-upper sequence corresponds to caccgGCCCACACGGGAGCGGAGAG (SEQ ID NO: 16), and DGCR8_sgRNA-lower sequence corresponds to aaacCTCTCCGCTCCCGTGTGGGCc (SEQ ID NO: 17). Referring to each of the listed sequences SEQ ID NO: 14 to SEQ ID NO: 17, the part indicated in capitals is a portion to substantially form a target sequence within mRNA.

Homology-directed repair template was prepared by repeating PCR, and then inserted into SalI- and NotI-digested pGL3-Basic plasmid (Promega, USA). CRISPR-Cas9-mediated 3×FLAG-2×Strep tag knock-in was implemented by co-transduction of CRISPR plasmid and HDR (homology-directed repair) template as described above. HEK293E cell was placed in a 6-well culture plate and incubated for 18 hours. 1 μg of CRISPR plasmid, 1 μg of HDR repair template and 2.5 μL of Lipofectamine 2000 were mixed in 100 μL of non-serum medium according to instructions of the manufacturer, followed by adding the same to cells contained in 900 μL of complete medium. After 3 days, with regard to DROSHA and DGCR8, respectively, random single cell sorting for 50 clones was implemented. Then, each clone was subjected to additional culture period for subsequent experiments.

6. PCR Assay of Genomic DNA

Using QuickExtract DNA Extraction Solution (Epicentre, USA), genomic DNA of each clone was extracted. The clone incubated in each 96-well plate was re-dispersed in 50 to 100 μL of QuickExtract solution and incubated at 65° C. for 30 minutes, and then at 95° C. for 30 minutes. The extracted genomic DNA was used as a template strand in subsequent PCR amplification. PCR amplification was performed at 95° C. for 5 minutes, [95° C. for 30 seconds, 60° C. for 30 seconds, and 72° C. for 1 minute]×35 cycles, and then, 72° C. for 5 minutes under a condition of thermal circulation. PCR primers for detection of DROSHA and DGCR8 were obtained by Genotech, Inc. (Korea). Specifically, a forward primer of DROSHA corresponds to SEQ ID NO: 19 (5'-CATCAGAAGCGGTTCATCGA-3') and a reverse primer thereof corresponds to SEQ ID NO: 20 (5'-AAGTAATGCA-CATTCACCAAAGTC-3'), while a forward primer of DGCR8 corresponds to SEQ ID NO: 21 (5'-GACTGTC-CATCACCACCAGA-3') and a reverse primer thereof corresponds to SEQ ID NO: 22 (5'-CAATGTGGCCAGCTTGACTA-3'). Sizes of PCR products were 514 base pairs (DROSHA-tag), 349 base pairs (DROSHA WT), 511 base pairs (Tag-DGCR8) and 322 base pairs (DGCR8 WT), respectively. Such PCR products were separated by electrophoresis in 1% agarose gel and detected by ChemiDoc MP System (Bio-rad, USA).

7. Sequencing Analysis

The obtained PCR product was purified using LaboPass gel extraction kit by instructions of the manufacturer (Cosmogenetech, Korea). The purified product was subjected to cloning by TOPcloner blunt core kit (Enzynomics, Korea), and then, proliferated in competent E. coli Stbl3 cell. Plasmid DNA was incubated in E. coli overnight by LaboPass plasmid mini-prep kit (Cosmogenetech Inc., Korea), followed by extraction. The purified plasmid DNA was subjected to sequencing by Cosmogenetech Inc., Korea).

8. Immune Precipitation-Western Blot (IP-WB) Assay and RNA-Seq Assay

100% cells were collected in a 100 mm culture dish and dissolved in RIPA buffer along with ultra-sonication (Thermo Fisher Scientific Inc., USA). According to instructions of the manufacturer, immune precipitation was performed using 1 mg of cell solvate and ANTI-FLAG M2 affinity gel (Sigma-Aldrich; Merck, Germany). IP sample including 50 μg (5%) of input sample was isolated in 8% SDS-PAGE gel and moved to Amersham Hybond ECL membrane (GE Healthcare, United Kingdom). Blots were probed into antibodies to DROSHA (Abcam, United Kingdom), DGCR8 (mouse monoclonal anti-DGCR8 antibody clone #19A1), FLAG (Sigma-Aldrich; Merck, Germany) and alpha-tubulin (Cell Signaling, USA), respectively. The antibodies were subjected to visualization using Amersham ECL Select western blot detection reagent (GE Healthcare, United Kingdom) and ChemiDoc MP System (Bio-rad, USA).

Further, mRNA expression level in HEK293T cell was determined in GEO: GSE93619 (a sample transduced into an empty vector).

Figure 7:
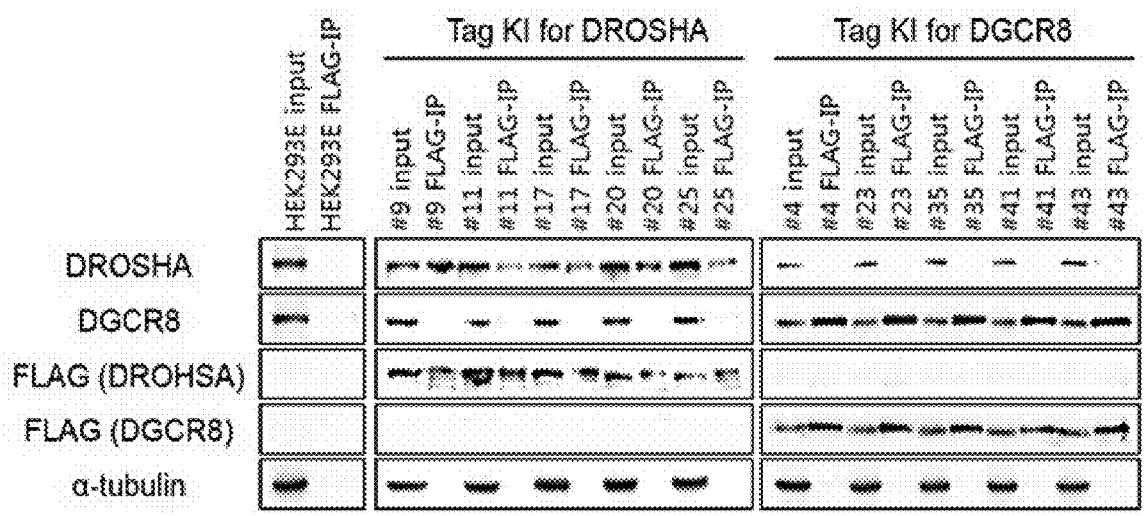
FIG. 7 is diagrams illustrating results of top 5 clones to tag mRNA inserted into each gene during screening based on Cy5-labeled GO-GEMS complex, wherein a of FIG. 7 illustrates a frequency of inserted allelic genes when analyzed by PCR cloning and bacteria colony sequencing, and b of FIG. 7 illustrates IP-WB assay results.

Experimental Result (1) After the additional incubation period, quantitative analysis of tag expression level was performed by GO-GEMS system. After screening three times using In Cell analyzer, a relative fluorescent intensity of the cell was determined (b of FIG. 2), and 5 clones having top 10% higher fluorescent signal intensities on average were selected from the tagged mRNA. Gene introduction of the selected clones was identified by PCR assay of genomic DNA (c of FIG. 2), sequencing and immune precipitation-western blot (IP-WB) assay (FIG. 7). It was confirmed that each clone contains at least one tagged allelic gene and expresses a target protein tagged without influence on other genes.

Referring to c of FIG. 2, band corresponding to DROSHA-tag and Tag-DGCR8 are determined as gene knock-in portions.

Specifically, a of FIG. 7 illustrates that the above 5 clones exhibiting top 10% higher fluorescent signal intensity were analyzed by PCR in order to determine a frequency of allelic genes inserted by bacteria colony sequencing. Further, it could be seen that 5 clones sorted with regard to each of DROSHA and DGCR8 have allelic genes, each of which contains at least one 3×FLAG-2×Strep tag.

Figure 8:
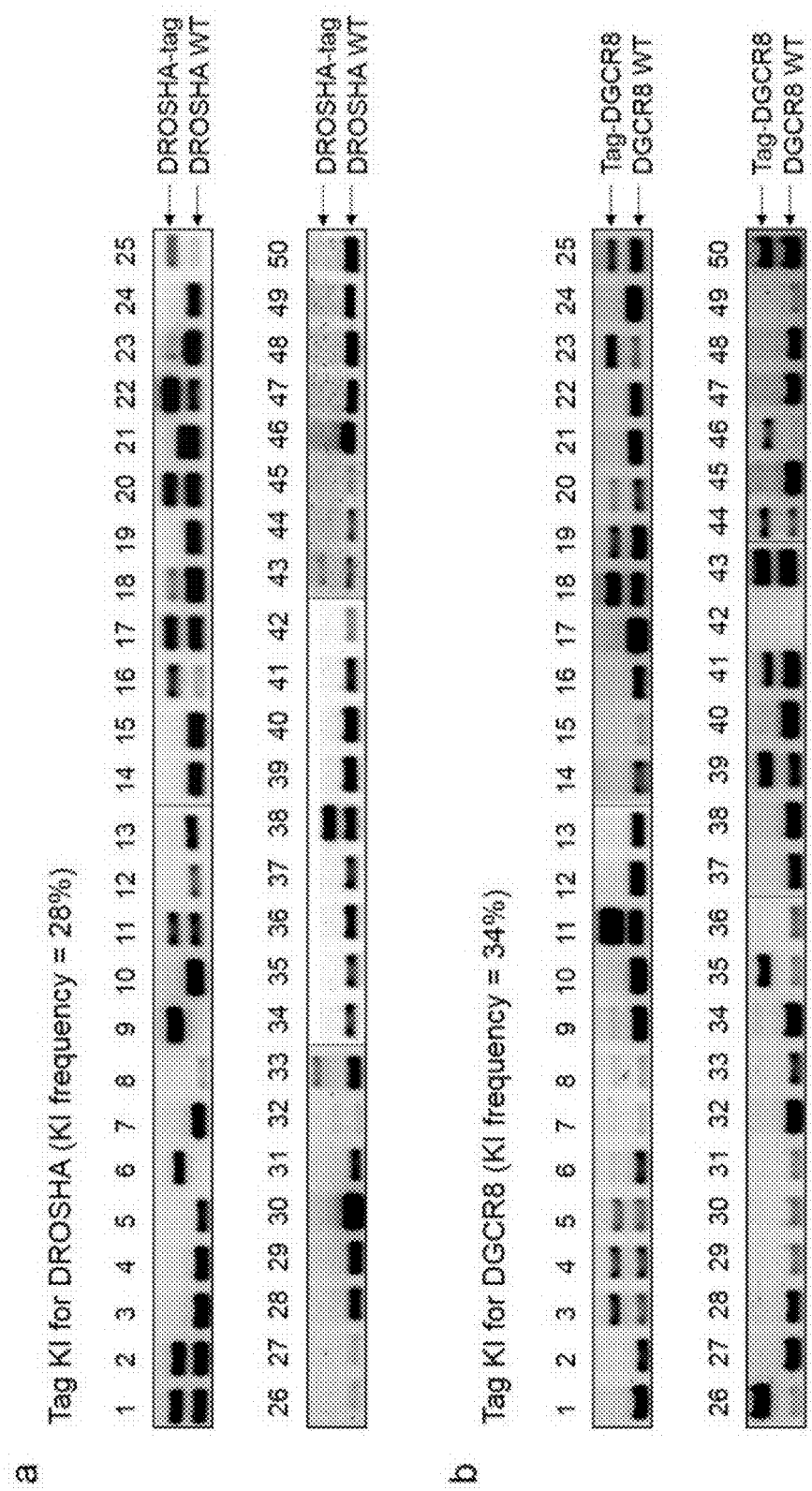
FIG. 8 is diagrams illustrating results of genomic DNA PCR assay for monocyte-derived clone of HEK293E by CRISPR-Cas9 mediated tag knock-in (that is, insertion), and demonstrating that GO-GEM screening result of transgenic cells is more effective and has higher reliability than the existing PCR assay results.

(2) As compared to the existing method based on PCR assay of genomic DNA (FIG. 8), the inventive method could produce positive clones abundantly at a frequency of 100%, which has a gene introduction frequency of 30% or less (e.g., the gene introduction frequency of 28% in a of FIG. 8 and 34% in b of FIG. 8).

Figure 9:
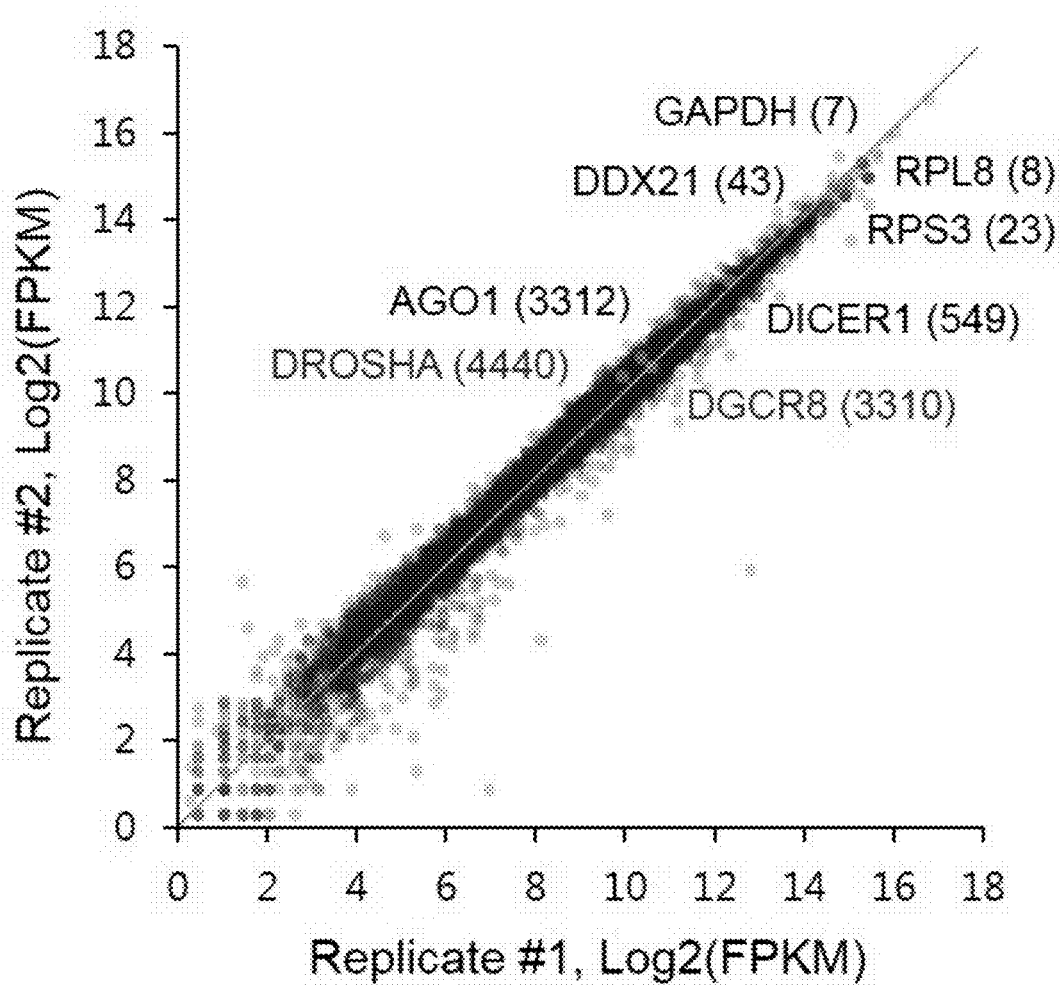
FIG. 9 is a diagram illustrating mRNA expression levels of different genes in HEK293T cell, and demonstrating that expression of genes such as DROSHA or DGCR8 could be efficiently analyzed by GO-GEMS application.

Further, although the expression levels of DROSHA and DGCR8 mRNA were considerably lower than high expression level genes such as GAPDH or ribosome protein, the present invention could efficiently analyze the above results, which in turn ensures a significant meaning of the present invention (FIG. 9). This demonstrates that the method according to the present invention achieves excellent mRNA detection performance.

A sequence listing electronically submitted with the present application on Sep. 15, 2020 as an ASCII text file named 20200915_Q16519LC37_TU_SEQ, created on Sep. 10, 2020 and having a size of 38,000 bytes, is incorporated herein by reference in its entirety.

What is claimed is:

1. A method for production of foreign gene-introduced cell, the method comprising:
   introducing a foreign gene into a target cell, the foreign genes configured to allow the target cells to generate a target material in the target cell by the introduction so that the foreign gene-introduced cells produce the target material;
   treating the foreign gene-introduced cell with a graphene oxide sensor in which a water-soluble polymer is bound to a carboxyl group portion of a surface thereof and a fluorescent conjugated probe is bound to the remaining portion of the surface to which the water-soluble polymer is not bound;
   detecting fluorescent emission in the cell; and
   incubating a cell in which emission is detected,
   wherein the probe is specifically bound to the target material produced in the target cell by introduction of the foreign gene,
   wherein the foreign gene introduction is performed using CRISPR-Cas9.

2. The method according to claim 1, wherein the water-soluble polymer is selected from the group consisting of chitosan, chitosan salts, dextran, hyaluronic acid, hyaluronic acid salts, pectin, pectin salts, alginate, alginic acid, agar, galactomannan, galactomannan salts, xanthan, xanthan salts, polyethyleneglycol (PEG), polyethyleneimine (PEI), and a combination thereof.

3. The method according to claim 1, wherein the graphene oxide is graphene oxide nanocolloids.

4. The method according to claim 1, wherein the graphene oxide is selected from the group consisting of nanographene oxide (NGO), a reduced graphene oxide, graphene oxide nanocolloids (GON), and a combination thereof.

5. The method according to claim 1, wherein the probe is any one selected from the group consisting of antibody, nucleic acid, peptide, protein and a combination thereof.

6. The method according to claim 1, wherein the target material is mRNA or miRNA.

7. The method according to claim 1, wherein the probe is peptide nucleic acid (PNA) specifically bound to the target material.

8. The method according to claim 1, wherein the target material is mRNA or miRNA, and the probe is peptide nucleic acid (PNA) specifically bound to the target material.

9. The method according to claim 1, wherein the target cell is selected from the group consisting of a cell of human, a cell of an animal other than human, a plant cell, and a cell of microorganism.

10. The method according to claim 1, wherein the target cell is at least one of a human uterine cervical cancer cell and a human embryonic renal cell.

11. A method for production of foreign gene-introduced cell, the method comprising:
   introducing a foreign gene into a target cell, the foreign genes configured to allow the target cells to generate a target material in the target cell by the introduction so that the foreign gene-introduced cells produce the target material;
   treating the foreign gene-introduced cell with a graphene oxide sensor in which a water-soluble polymer is bound to a carboxyl group portion of a surface thereof and a fluorescent conjugated probe is bound to the remaining portion of the surface to which the water-soluble polymer is not bound;
   detecting fluorescent emission in the cell; and
   incubating a cell in which emission is detected,
   wherein the probe is specifically bound to the target material produced in the target cell by introduction of the foreign gene,
   wherein the introducing of the foreign gene into the target cell comprises tag-inserting the foreign gene at the C-terminus of DROSHA or the N-terminus of DGCR8 (DiGeorge syndrome critical region gene 8).

12. The method according to claim 1, wherein the target material is selected from the group consisting of a protein, a hormone, a hormone-like substance, an enzyme, an enzyme inhibitor, a signal transduction protein, an antibody, a monoclonal antibody, a binder protein, a binder domain, a peptide, antigen, a metabolic material, a membrane protein, a receptor protein, an adherence protein, a structural protein, a regulatory protein, a toxin protein, a growth factor, a cytokine, a transcription factor, a coagulation factor, and a plant bio-based resistance inducer protein.

13. The method according to claim 11, wherein the water-soluble polymer is selected from the group consisting of chitosan, chitosan salts, dextran, hyaluronic acid, hyaluronic acid salts, pectin, pectin salts, alginate, alginic acid, agar, galactomannan, galactomannan salts, xanthan, xanthan salts, polyethyleneglycol (PEG), polyethyleneimine (PEI), and a combination thereof.

14. The method according to claim 11, wherein the graphene oxide is selected from the group consisting of nanographene oxide (NGO), a reduced graphene oxide, graphene oxide nanocolloids (GON), and a combination thereof.

15. The method according to claim 11, wherein the foreign gene introduction is performed by transformation, transfection, transduction, gene transfer, conjugation or gene scissors.

16. The method according to claim 11, wherein the foreign gene introduction is performed using CRISPR-Cas9.

17. The method according to claim 11, wherein the probe is any one selected from the group consisting of antibody, nucleic acid, peptide, protein and a combination thereof.

18. The method according to claim 11, wherein the target material is mRNA or miRNA.

19. The method according to claim 11, wherein the target cell is at least one of a human uterine cervical cancer cell and a human embryonic renal cell.

20. The method according to claim 11, wherein the target material is selected from the group consisting of a protein, a hormone, a hormone-like substance, an enzyme, an enzyme inhibitor, a signal transduction protein, an antibody, a monoclonal antibody, a binder protein, a binder domain, a peptide, antigen, a metabolic material, a membrane protein, a receptor protein, an adherence protein, a structural protein, a regulatory protein, a toxin protein, a growth factor, a cytokine, a transcription factor, a coagulation factor, and a plant bio-based resistance inducer protein.

* * * * *

```
                         SEQUENCE LISTING

<160> NUMBER OF SEQ ID NOS: 22

<210> SEQ ID NO 1
<211> LENGTH: 19
<212> TYPE: DNA
<213> ORGANISM: Artificial Sequence
<220> FEATURE:
<223> OTHER INFORMATION: GAPDH target PNA probe

<400> SEQUENCE: 1
gagtccttcc acgatacca                                                   19

<210> SEQ ID NO 2
<211> LENGTH: 19
<212> TYPE: DNA
<213> ORGANISM: Artificial Sequence
<220> FEATURE:
<223> OTHER INFORMATION: EGFP target PNA probe

<400> SEQUENCE: 2
aagtcgtgct gcttcatgt                                                   19

<210> SEQ ID NO 3
<211> LENGTH: 19
<212> TYPE: DNA
<213> ORGANISM: Artificial Sequence
<220> FEATURE:
<223> OTHER INFORMATION: RFP target PNA probe

<400> SEQUENCE: 3
ttcttggatc tgtatgtgg                                                   19

<210> SEQ ID NO 4
<211> LENGTH: 19
<212> TYPE: DNA
<213> ORGANISM: Artificial Sequence
<220> FEATURE:
<223> OTHER INFORMATION: 3xFLAG-2xStrep tag target PNA probe
```

```
<400> SEQUENCE: 4
gtggctccaa gcagatcct                                                       19

<210> SEQ ID NO 5
<211> LENGTH: 19
<212> TYPE: DNA
<213> ORGANISM: Artificial Sequence
<220> FEATURE:
<223> OTHER INFORMATION: 3xFLAG-2xStrep tag target PNA probe

<400> SEQUENCE: 5
cgcccttctc aaactgagg                                                       19

<210> SEQ ID NO 6
<211> LENGTH: 19
<212> TYPE: DNA
<213> ORGANISM: Artificial Sequence
<220> FEATURE:
<223> OTHER INFORMATION: 3xFLAG-2xStrep tag target PNA probe

<400> SEQUENCE: 6
tgtagtcgat gtcgtgatc                                                       19

<210> SEQ ID NO 7
<211> LENGTH: 22
<212> TYPE: DNA
<213> ORGANISM: Artificial Sequence
<220> FEATURE:
<223> OTHER INFORMATION: scrambled target PNA probe

<400> SEQUENCE: 7
atcgaatagt ctgactacaa ct                                                   22

<210> SEQ ID NO 8
<211> LENGTH: 5424
<212> TYPE: DNA
<213> ORGANISM: Homo sapiens

<400> SEQUENCE: 8
accgcgcaca aggccctgcg gtgggctgaa gagttttccc tcccttggcc cagctttctc          60
aggtttgctt tttaattccc tcggtttcct gttccggagg cgcgggcggt gccactgtct         120
tggtacctgc ggtagtagcc tggctttgct ctgacgcgca tctcgcggcc cgagagcctt         180
ttataggttg cttttcccgg ggatgtgaag gatacagaaa tgactgtgaa tcaacccata         240
tcatcaagga gctgataatc tagtggaaga gttagacgtg tgcatacttc actatgatat         300
gaggcagtct ctgagcttat attctctgtg gaagatgtga catatccagg cggaacatca         360
tgatgcagga aaacacatgt cacagaatgt cgttccaccc gggacgaggg tgtcccgag          420 gacgaggagg acatggagcc agaccctcag caccatcctt taggccccaa aatctgaggc         480
tgcttcaccc tcagcagcct cctgtgcaat atcaatatga acctccaagt gcccttcca          540 ccactttctc aaactctcca gcccccaatt ttctccctcc acgaccagac tttgtaccct         600
tccccccacc catgcctccg tcagcgcaag gccctcttcc ccctgcccaa atcaggccgc         660
ctttcccaaa ccaccagatg aggcacccct tcccagttcc tccttgtttt cctcccatgc         720
caccaccaat gccttgtcct aataaccccc cagtccctgg ggcacctcct ggacaaggca         780 ctttccccctt catgatgccc cctccctcca tgcctcatcc ccgcccccct ccagtcatgc        840
cgcagcaggt taattatcag taccctccgg gctattctca ccacaacttc ccacctccca        900
```

```
gttttaatag tttccagaac aaccctagtt cttttcctgcc cagtgctaat aacagcagta    960
gtcctcattt cagacatctc cctccatacc cactcccaaa ggctcccagt gagagaaggt   1020
ccccagaaag gctgaaacac tatgatgacc acaggcaccg agatcacagt catgggcgag   1080
gtgagaggca tcggtccctg gatcggcggg agcgaggccg cagtcccgac aggagaagac   1140
aagacagccg gtacagatct gattatgacc gagggagaac accatctcgc caccgcagct   1200
acgaacggag cagagagcga gaacgggaga gacacaggca tcgagacaac cgaagatcac   1260
catctctgga aaggtcctac aaaaaagagt ataagagatc tggaaggagt tacggtttat   1320
cggttgttcc tgaacctgct ggatgcacac cagaattacc tggggagatt attaaaaata   1380
cagattcttg ggccccaccc ctggagattg tgaatcatcg ctccccaagt agggagaaga   1440
agagagctcg ttgggaggaa gaaaaagacc gttggagtga caaccagagt tctggcaaag   1500
acaagaacta tacctcaatc aaggaaaaag agcccgagga gaccatgcct gacaagaatg   1560
aggaggaaga agaagaactt cttaagcctg tgtggattcg atgcactcat tcagaaaact   1620
actactccag tgacccatg gatcaggtgg agagattctac agtggttgga acgagtaggc   1680
ttcgtgactt atatgacaaa tttgaggagg agttggggag caggcaagaa aaggccaaag   1740
ctgctcggcc tccgtgggaa cctccaaaga cgaagctcga tgaagattta gagagttcca   1800
gtgaatccga gtgtgagtct gatgaggaca gcacctgttc tagcagctca gactctgaag   1860
tttttgacgt tattgcagaa atcaaacgca aaaaggccca ccctgaccga cttcatgatg   1920
aactttggta caacgatcca ggccagatga atgatggacc actctgcaaa tgcagcgcaa   1980
aggcaagacg cacaggaatt aggcacagca tttatcctgg agaagaggcc atcaagccct   2040
gtcgtcctat gaccaacaat gctggcagac ttttccacta ccggatcaca gtctccccgc   2100
ctacgaactt tttaactgac aggccaactg ttatagaata cgatgatcac gagtatatct   2160
ttgaaggatt ttctatgttt gcacatgccc ccctgaccaa tattccactg tgtaaagtaa   2220
ttagattcaa catagactac acgattcatt tcattgaaga gatgatgccg gagaattttt   2280
gtgtgaaagg gcttgaactc ttttcactgt tcctattcag agatattttg gaattatatg   2340
actggaatct taaaggtcct ttgtttgaag acagccctcc ctgctgccca agatttcatt   2400
tcatgccacg ttttgtaaga tttcttccag atggaggaaa ggaagtgctg tccatgcacc   2460
agattctcct gtacttgtta aggtgcagca aagccctggt gcctgaggag gagattgcca   2520
atatgcttca gtgggaggag ctggagtggc agaaatatgc agaagaatgc aaaggcatga   2580
ttgttaccaa ccctgggacg aaaccaagct ctgtccgtat cgatcaactg gatcgtgaac   2640
agttcaaccc cgatgtgatt acttttccga ttatcgtcca ctttgggata cgccctgcac   2700
agttgagtta tgcaggagac ccacagtacc aaaaactgtg gaagagttat gtgaaacttc   2760
gccacctcct agcaaatagt cccaaagtca acaaactga caaacagaag ctggcacaga   2820
gggaggaagc cctccaaaaa atacggcaga agaatacaat gagacgagaa gtaacggtgg   2880
agctaagtag ccaaggattc tggaaaactg gcatccgttc tgatgtctgt cagcatgcaa   2940
tgatgctacc tgttctgacc catcatatcc gctaccacca atgcctaatg catttggaca   3000
agttgatagg atatactttc caagatcgtt gtctgttgca gctggccatg actcatccaa   3060
gtcatcattt aaattttgga atgaatcctg atcatgccag gaattcatta tctaactgtg   3120
gaattcggca gccaaatac ggagacagaa aagttcatca catgcacatg cggaagaaag   3180
ggattaacac cttgataaat atcatgtcac gccttggcca agatgaccca actccctcga   3240
ggattaacca caatgaacgg ttggaattcc tgggtgatgc tgttgttgaa tttctgacca   3300
```

```
gcgtccattt gtactatttg tttcctagtc tggaagaagg aggattagca acctatcgga   3360
ctgccattgt tcagaatcag caccttgcca tgctagcaaa gaaacttgaa ctggatcgat   3420
ttatgctgta tgctcacggg cctgaccttt gtagagaatc ggaccttcga catgcaatgg   3480
ccaattgttt tgaagcgtta ataggagctg tttacttgga gggaagcctg gaggaagcca   3540
agcagttatt tggacgcttg ctctttaatg atccggacct gcgcgaagtc tggctcaatt   3600
atcctctcca cccactccaa ctacaagagc caaatactga tcgacaactt attgaaactt   3660
ctccagttct acaaaaactt actgagtttg aagaagcaat tggagtaatt tttactcatg   3720
ttcgacttct ggcaagggca ttcacattga gaactgtggg atttaaccat ctgaccctag   3780
gccacaatca gagaatggaa ttcctaggtg actccataat gcaactggta gccacagagt   3840
acttattcat tcatttccca gatcatcatg aaggacactt aactttgttg cgaagctctt   3900
tggtgaataa tagaactcag gccaaggtag cggaggagct gggcatgcag gagtacgcca   3960
taaccaacga caagaccaag aggcctgtgg cgcttcgcac caagaccttg gcggaccttt   4020
tggaatcatt tattgcagcg ctgtacattg ataaggattt ggaatatgtt catactttca   4080
tgaatgtctg cttcttttcca cgattgaaag agttcatttt gaatcaggat tggaatgacc   4140
ccaaatccca gcttcagcag tgttgcttga cacttaggac agaaggaaaa gagccagaca   4200
ttcctctgta caagactctg cagacagtgg gcccatccca tgcccgaacc tacactgtgg   4260
ctgtttattt caagggagaa agaataggct gtgggaaagg accaagtatt cagcaagcgg   4320
aaatgggagc agcaatggat gcgcttgaaa aatataattt tccccagatg gcccatcaga   4380
agcggttcat cgaacggaag tacagacaag agttaaaaga aatgaggtgg gaaagagagc   4440
atcaagagag agagccagat gagactgaag acatcaagaa ataaggagg gcatgcaagt   4500
gtggagtatt tacttgctca gtaactgtga ctgttgtcta ttgagaccta gcctagtttt   4560
cctgcagaca atgaatgaag tgtgctcatt gaaataaaat acagagtcaa atcgctattg   4620
ttgttttaat gatctgtttt tagctggatg gtctttatta caaagtatta gattttctctt   4680
ctatttaacg gaaaacttga ctttggtgaa tgtgcattac ttcctttat tttgctcttt   4740
aaataataaa attcaagaag catattctat gtggaataga tcctgttttt ccatctgtgt   4800
cccagattgt gacccctagac tttcaattga caagtaaaaa attgacttta ctagacattt   4860
tgactgtgct ctagtaacat ctatccttt tcaaatctct ggattttaa gtagattgtt   4920
cagctttcat ccggtggctg ttcatcaagt tatcagctgc aaatattgaa cttacctctc   4980
tctaagcagt gagtgttttg tagaaggaat ccgtttaaca attaattggc taatgggaga   5040
agggaaaga ctgatattca agtcatacag attctttgaa tcattagaat aggagagaaa   5100
tcatgattct aagccaggcc acactttaaa ccaagtgctc tcaccctggg gttagtggaa   5160
cctttaagaa gttaatgaac agacttcaag gaagtcaaaa acctcccaat actatattca   5220
attttctgtg tgtgtttgag atttgagagg gcatggggag caggaaggag gagggtttat   5280
agcttttatc agcctctcta agtgggccct gcagtaaaag gctaacatga cattcaaaga   5340
cataacattt taaaaaaagt tattccaaac taaacatcac tggtttctta ttaataaagg   5400
caaaacttct ttgtaaaaca aaaa                                         5424

<210> SEQ ID NO 9
<211> LENGTH: 4536
<212> TYPE: DNA
<213> ORGANISM: Homo sapiens
```

```
<400> SEQUENCE: 9
aggcccgccc tccgctcgcc cggcgcggca ggcgggtgcc ggcgaccgga gagcctggac      60
aggcttttcca gatggctgcg gcggtcggtc ggtgaggctt cccggctgt ggtttggctg     120
cgggcggctt gggcagcccg cgggcgcctc aggtagaaga agaaaggtgc cactccggca     180
tgaagacaga ctcgcttagt cgccagtcac ttaagctgag tgcattgtga tttccaataa     240
ttgaggcagt ggttctaaaa gctgtctaca ttaatgaaaa gagcaatgtg ccagcttga      300
ctaagccgcc agcgcacagc gcggcaggac gcgcccgggt ctcagcggac ttgtgcatgt     360
tagctgtgta gatttatgtg agggcttgta aaactctggt cttgtaaact agtcttaagc     420
gcttttaata tggagacaga tgagagcccc tctccgctcc cgtgtgggcc cgcaggagaa     480
gcggtgatgg agagccgagc tcgccccttc caagcgctgc cccgtgagca gtctccacca     540
cctcccctgc aaacgtccag tggtgcagag gtaatggacg ttggctctgg tggtgatgga     600
cagtccgaac tccctgctga ggacccctt aacttctacg gagcttctct tctctccaaa      660
ggatccttct ctaagggccg cctcctcata gacccgaact gtagtggcca cagcccgcgc     720
accgcccggc acgcacctgc ggtccggaag ttctcccctg accttaagtt gcttaaggat     780
gtaaagatta gcgtgagctt taccgagagc tgcaggagta aggacaggaa ggtgctgtac     840
acaggagcag agcgcgacgt gcgggcggag tgcggtctgc tccttagccc tgtcagtggg     900
gacgtgcatg cttgtccctt tggcgggagt gttggtgacg gggtaggcat aggggggtgag    960
agtgctgata agaaggatga ggagaatgag ctggatcagg aaaagagagt ggagtatgca    1020
gtgctcgatg agttagaaga ttttactgac aatttggagc tagatgaaga aggagcaggc    1080
gggttcacgg ctaaagcaat cgttcagaga gacagagtgg atgaagaggc cttgaatttc    1140
ccctacgagg atgactttga caacgatgtg gatgctctgc tggaagaagg cctttgtgcc    1200
cccaaaaaga ggcgaacaga ggaaaaatat ggcggagaca gcgaccatcc gtccgatgga    1260
gagacaagtg tgcagccgat gatgaccaag attaaaacag tgctcaaaag tcgtggccgc    1320
ccacctacag agccgctgcc cgacgggtgg atcatgacat tccataactc tggagtcccg    1380
gtgtacctac acagagagtc tcgggtggtc acctggtcca ggccatactt cttgggaacg    1440
ggaagcatac ggaaacacga ccctcctctg agtagcatcc cttgtctgca ttataagaaa    1500
atgaaggaca cgaggaacg ggagcaaagc agtgacctca cccctagtgg ggatgtgtcc     1560
cccgtcaagc ccctgagccg atctgcagag ctggagtttc ccctggatga gcctgactct    1620
atgggtgctg acccgggggcc cccggacgag aaagacccac taggggctga ggcagccct    1680
ggggccctgg ggcaggtgaa ggccaaagtc gaggtgtgca agatgaatc cgttgatctc    1740
gaggaatttc gaagctacct ggagaagcgt tttgactttg agcaagttac tgtgaaaaaa    1800
ttcaggactt gggctgagcg gcggcaattc aatcgggaaa tgaagcggaa gcaggcggag    1860
tccgagaggc ccatcttgcc agccaatcag aagctcatta ctttatcagt gcaagatgca    1920
cccacaaaga aagagtttgt tattaacccc aacgggaaat ccgaggtctg catcctgcac    1980
gagtacatgc agcgtgtcct caaggtccgc cctgtctata atttctttga atgtgagaac    2040
ccaagtgagc cttttggtgc ctcggtgacc attgatggtg tgacttacgg atctggaact    2100
gcaagcagca aaaaacttgc gaagaataaa gctgcccgag ctacactgga aatcctcatc    2160
cctgactttg ttaaacagac ctctgaagag aagcccaaag acagtgaaga actcgagtat    2220
tttaaccaca tcagcatcga ggactcgcgg gtctacgagc tgaccagcaa ggctgggctg    2280
ttgtctccat atcagatcct ccacgagtgc cttaaaagaa accatgggat gggtgacacg    2340
```

```
tctatcaagt tgaagtggt tcctgggaaa aaccagaaga gtgaatacgt catggcgtgt    2400
ggcaagcaca cagtgcgcgg gtggtgtaag aacaagagag ttggaaagca gttagcctca    2460
cagaagatcc ttcagctgct gcacccacat gtcaagaact gggggtcttt actgcgcatg    2520
tatggccgtg agagcagcaa gatggtcaag caggagacat cggacaagag tgtgattgag    2580
ctgcagcagt atgccaagaa gaacaagccc aacctgcaca tcctcagcaa gctccaagag    2640
gagatgaaga ggctagctga ggaaagggag gagactcgaa agaagcccaa gatgtccatt    2700
gtggcgtccg cccagcctgg cggtgagccc ctgtgcaccg tggacgtgtg agggaggtgg    2760
cacgggccag ggcgcggggg ccgccagccg cacttctgag gagaccagca gtcatgcatc    2820
gtgcaccaca gtgtcaggcc tccaacccac gctccttccc tgtggccaac ctgtgggccc    2880
ggccttaggg tggaggcttt agtgtacagg gacagccatg ccacacagc acacatgtgg     2940 agcagcggct ctccctggaa agctccaggc ctgaatggat ggactcagcg actgcaccag    3000
tggcagctgg tgactgtgga cagtggtgga ccctgcttct gtgcacctgc tgcaggctct    3060
ttttatgaag gctttcatga attttagtat gtaatacgca ctgacgacac atgatgcttg    3120
gatgacagat gagaggggat ggctgagtcc tgtggctggc ccgtgatgcc aggtggccca    3180
tgtgcccagg gcgcctgcag ggctgctaca gggacctggt caggaggtgc acatggtgcc    3240
ctgccctcac ccaccctctg tgtttcccct tctttgaaaa ggtagaagag aaaggaatat    3300
tttaaacctt tttggcttaa acagaatttt agcatcagaa ctagctttct gggattggag    3360
gcaaaccatc aaggtggtcc ctctccagtc tggacacgat gccagcaagg atgacgtcct    3420
gccacctcct ggagttaccc tggcctccta gggtcccttt ttctgatgaa gtcttaattc    3480
cctaaaagcg cctctttgga cactgaggcc ctctctgcct ttcctggcct ccggcaacag    3540
ttttttacaa agatttttg cagtcgagtc catatgtcca cccattgatt tttaaagctt     3600
ttgtgatatt ttagcatttt gaaagacttt cacagtgaga gtagaaggta gatttggaat    3660
catgcatttt agcaagtgga cttgttgaaa caggaagcaa gggccttcag tgtagcccat    3720
tcttgatcca gagctgttgc ctgtgacagc ggtttctctg gatgtcaaag gcagctgcct    3780 ggtgccagc ttgcttctcg actggtggcc cctatgggtg ggtgtgcgat ggaaatgtgt     3840
tcctgccgga gtctgaggca ccagggtgtg ctcaaaggct ggccctggtg gtggactggc    3900
acctgtgcag agtgccgtgt gcttgtggtg cgccatctga agcaagagtc cagcgttctg    3960
ccgtgtctgt cccccaccat gcccctaca ggcggtactg atggcgcttt ttttttttt     4020 tctgtcagga aaacaatgtt ggcctgtggg ccgcccacaa catatccttc cctcactacc    4080
tgtgtgacca aggttggctt ctgttgacct ttaaaaaaga aaccctcaac tcaaattgct    4140
ataattagac acttgcttct gtcttgcctc ctgtctgcag ctgtgaatag tcatttgact    4200
gtgactgttg cccttagcca gccagatgcg cctgtgaacc aaagcttcgt gcacatgtgt    4260 tccctaaag gttggggagc ctcgctgtgt cttgctgttc ccaggcacca ccacagcagg     4320
tgctgccata ctcttgtggt ctctgtgcgc ccccccccc cccccacccg tctgccaagc     4380
atgggtatga atcgtgcaca cagccatgct tcaaggccgg ggcaggggag cctgtgctga    4440
tgccatccag ggcactgggc tgtgcctgga aggcgagcct tgattgtctg aacacataaa    4500
gcaaactgtc cagaagggaa aaaaaaaaaa aaaaaa                              4536
```

<210> SEQ ID NO 10
<211> LENGTH: 4725
<212> TYPE: DNA

<213> ORGANISM: Artificial Sequence
<220> FEATURE:
<223> OTHER INFORMATION: knockin 3xFLAG-2xStrep tag

<400> SEQUENCE: 10

```
aggcccgccc tccgctcgcc cggcgcggca ggcgggtgcc ggcgaccgga gagcctggac      60
aggcttttcca gatggctgcg gcggtcggtc ggtgaggctt tcccggctgt ggtttggctg    120
cgggcggctt gggcagcccg cgggcgcctc aggtagaaga agaaaggtgc cactccggca    180
tgaagacaga ctcgcttagt cgccagtcac ttaagctgag tgcattgtga tttccaataa    240
ttgaggcagt ggttctaaaa gctgtctaca ttaatgaaaa gagcaatgtg gccagcttga    300
ctaagccgcc agcgcacagc gcggcaggac gcgcccgggt ctcagcggac ttgtgcatgt    360
tagctgtgta gatttatgtg agggcttgta aaactctggt cttgtaaact agtcttaagc    420
gcttttaatg ccaccatggg atccgccggc gactacaagg accacgacgg cgattataag    480
gatcacgaca tcgactacaa agacgacgat gacaagggcg ccagcagcgc ctggtcccac    540
cctcagtttg agaagggcgg aggctctggc ggcgaagcg gaggatctgc ttggagccac    600
ccccagttcg aaaagggcgc cgagacagat gagagcccct tccgctcccg tgtgggccc     660
gcaggagaag cggtgatgga gagccgagct cgccccttcc aagcgctgcc ccgtgagcag    720
tctccaccac ctcccctgca aacgtccagt ggtgcagagg taatggacgt tggctctggt    780
ggtgatggac agtccgaact ccctgctgag gaccccttca acttctacgg agcttctctt    840
ctctccaaag gatccttctc taagggccgc ctcctcatag acccgaactg tagtggccac    900
agcccgcgca ccgcccggca cgcacctgcg gtccggaagt tctcccctga ccttaagttg    960
cttaaggatg taaagattag cgtgagcttt accgagagct gcaggagtaa ggacaggaag   1020
gtgctgtaca caggagcaga gcgcgacgtg cgggcggagt gcggtctgct ccttagccct   1080
gtcagtgggg acgtgcatgc ttgtcccttt ggcgggagtg ttggtgacgg ggtaggcata   1140
gggggtgaga gtgctgataa gaaggatgag gagaatgagc tggatcagga aaagagagtg   1200
gagtatgcag tgctcgatga gttagaagat tttactgaca atttggagct agatgaagaa   1260
ggagcaggcg ggttcacggc taaagcaatc gttcagagag acagagtgga tgaagaggcc   1320
ttgaatttcc cctacgagga tgactttgac aacgatgtgg atgctctgct ggaagaaggc   1380
ctttgtgccc ccaaaaagag gcgaacagag gaaaaatatg gcggagacag cgaccatccg   1440
tccgatggag agacaagtgt gcagccgatg atgaccaaga ttaaaacagt gctcaaaagt   1500
cgtggccgcc cacctacaga gccgctgccc gacgggtgga tcatgacatt ccataactct   1560
ggagtcccgg tgtacctaca cagagagtct cgggtggtca cctggtccag gccatacttc   1620
ttgggaacgg gaagcatacg gaaacacgac cctcctctga gtagcatccc ttgtctgcat   1680
tataagaaaa tgaaggacaa cgaggaacgg gagcaaagca gtgacctcac ccctagtggg   1740
gatgtgtccc ccgtcaagcc cctgagccga tctgcagagc tggagttcc cctggatgag   1800
cctgactcta tgggtgctga cccggggccc ccggacgaga aagacccact aggggctgag   1860
gcagcccctg ggccctgggg caggtgaag gccaaagtcg aggtgtgcaa agatgaatcc   1920
gttgatctcg aggaatttcg aagctacctg gagaagcgtt ttgactttga gcaagttact   1980
gtgaaaaaat tcaggacttg gctgagcgg cggcaattca atcgggaaat gaagcggaag   2040
caggcggagt ccgagaggcc catcttgcca gccaatcaga agctcattac tttatcagtg   2100
caagatgcac ccacaaagaa agagtttgtt attaaccccca acgggaaatc cgaggtctgc   2160
atcctgcacg agtacatgca gcgtgtcctc aaggtccgcc ctgtctataa tttctttgaa   2220
```

```
tgtgagaacc caagtgagcc ttttggtgcc tcggtgacca ttgatggtgt gacttacgga    2280
tctggaactg caagcagcaa aaaacttgcg aagaataaag ctgcccgagc tacactggaa    2340
atcctcatcc ctgactttgt taaacagacc tctgaagaga agcccaaaga cagtgaagaa    2400
ctcgagtatt ttaaccacat cagcatcgag gactcgcggg tctacgagct gaccagcaag    2460
gctgggctgt tgtctccata tcagatcctc cacgagtgcc ttaaaagaaa ccatgggatg    2520
ggtgacacgt ctatcaagtt tgaagtggtt cctgggaaaa accagaagag tgaatacgtc    2580
atggcgtgtg gcaagcacac agtgcgcggg tggtgtaaga acaagagagt tggaaagcag    2640
ttagcctcac agaagatcct tcagctgctg cacccacatg tcaagaactg ggggtcttta    2700
ctgcgcatgt atggccgtga gagcagcaag atggtcaagc aggagacatc ggacaagagt    2760
gtgattgagc tgcagcagta tgccaagaag aacaagccca acctgcacat cctcagcaag    2820
ctccaagagg agatgaagag gctagctgag gaaagggagg agactcgaaa gaagcccaag    2880
atgtccattg tggcgtccgc ccagcctggc ggtgagcccc tgtgcaccgt ggacgtgtga    2940
gggaggtggc acgggccagg gcgcgggggc cgccagccgc acttctgagg agaccagcag    3000
tcatgcatcg tgcaccacag tgtcaggcct ccaacccacg ctccttccct gtggccaacc    3060
tgtgggcccg gccttagggt ggaggcttta gtgtacaggg acagccatgg ccacacagca    3120
cacatgtgga gcagcggctc tccctggaaa gctccaggcc tgaatggatg gactcagcga    3180
ctgcaccagt ggcagctggt gactgtggac agtggtggac cctgcttctg tgcacctgct    3240
gcaggctctt tttatgaagg ctttcatgaa ttttagtatg taatacgcac tgacgacaca    3300
tgatgcttgg atgacagatg agaggggatg gctgagtcct gtggctggcc cgtgatgcca    3360
ggtggcccat gtgcccaggg cgcctgcagg gctgctacag ggacctggtc aggaggtgca    3420
catggtgccc tgccctcacc caccctctgt gtttcccctt ctttgaaaag gtagaagaga    3480
aaggaatatt ttaaaccttt ttggcttaaa cagaatttta gcatcagaac tagctttctg    3540
ggattggagg caaaccatca aggtggtccc tctccagtct ggacacgatg ccagcaagga    3600
tgacgtcctg ccacctcctg gagttaccct ggcctcctag ggtccctttt tctgatgaag    3660
tcttaattcc ctaaaagcgc ctctttggac actgaggccc tctctgcctt tcctggcctc    3720
cggcaacagt tttttacaaa gatttttttgc agtcgagtcc atatgtccac ccattgattt    3780
ttaaagcttt tgtgatattt tagcattttg aaagactttc acagtgagag tagaaggtag    3840
atttggaatc atgcatttta gcaagtggac ttgttgaaac aggaagcaag ggccttcagt    3900
gtagcccatt cttgatccag agctgttgcc tgtgacagcg gtttctctgg atgtcaaagg    3960
cagctgcctg gtgcccagct tgcttctcga ctggtggccc ctatgggtgg gtgtgcgatg    4020
gaaatgtgtt cctgccggag tctgaggcac cagggtgtgc tcaaaggctg ccctggtgg    4080 tggactggca cctgtgcaga gtgccgtgtg cttgtggtgc gccatctgaa gcaagagtcc    4140
agcgttctgc cgtgtctgtc ccccaccatg cccctacag gcggtactga tggcgctttt    4200
tttttttttt ctgtcaggaa acaatgttg gcctgtgggc cgcccacaac atatccttcc    4260
ctcactacct gtgtgaccaa ggttggcttc tgttgacctt taaaaaagaa accctcaact    4320
caaattgcta taattagaca cttgcttctg tcttgcctcc tgtctgcagc tgtgaatagt    4380
catttgactg tgactgttgc ccttagccag ccagatgcgc ctgtgaacca aagcttcgtg    4440
cacatgtgtt cccctaaagg ttggggagcc tcgctgtgtc ttgctgttcc caggcaccac    4500
cacagcaggt gctgccatac tcttgtggtc tctgtgcgcc cccccccccc ccccaccgt    4560
```

-continued

```
ctgccaagca tgggtatgaa tcgtgcacac agccatgctt caaggccggg gcaggggagc    4620
ctgtgctgat gccatccagg gcactgggct gtgcctggaa ggcgagcctt gattgtctga    4680
acacataaag caaactgtcc agaagggaaa aaaaaaaaaa aaaaa                    4725
```

```
<210> SEQ ID NO 11
<211> LENGTH: 4725
<212> TYPE: DNA
<213> ORGANISM: Artificial Sequence
<220> FEATURE:
<223> OTHER INFORMATION: 3xFLAG-2xStrep knockin DGCR8 mRNA sequence

<400> SEQUENCE: 11
```

```
aggcccgccc tccgctcgcc cggcgcggca ggcgggtgcc ggcgaccgga gagcctggac      60 aggcttttcca gatggctgcg gcggtcggtc ggtgaggctt tcccggctgt ggtttggctg    120
cgggcggctt gggcagcccg cgggcgcctc aggtagaaga agaaaggtgc cactccggca    180
tgaagacaga ctcgcttagt cgccagtcac ttaagctgag tgcattgtga tttccaataa    240
ttgaggcagt ggttctaaaa gctgtctaca ttaatgaaaa gagcaatgtg ccagcttga     300 ctaagccgcc agcgcacagc gcggcaggac gcgcccgggt ctcagcggac ttgtgcatgt    360
tagctgtgta gatttatgtg agggcttgta aaactctggt cttgtaaact agtcttaagc    420
gcttttaatg ccaccatggg atccgccggc gactacaagg accacgacgg cgattataag    480
gatcacgaca tcgactacaa agacgacgat gacaagggcg ccagcagcgc ctggtcccac    540
cctcagtttg agaagggcgg aggctctggc ggcggaagcg gaggatctgc ttggagccac    600
ccccagttcg aaaagggcgc cgagacagat gagagcccct ctccgctccc gtgtgggccc    660
gcaggagaag cggtgatgga gagccgagct cgccccttcc aagcgctgcc ccgtgagcag    720
tctccaccac ctccctgca aacgtccagt ggtgcagagg taatgacgt tggctctggt     780 ggtgatggac agtccgaact ccctgctgag gaccccttca acttctacgg agcttctctt    840
ctctccaaag gatcctttc taagggccgc ctcctcatag acccgaactg tagtggccac    900
agcccgcgca ccgcccggca cgcacctgcg gtccggaagt tctcccctga ccttaagttg    960
cttaaggatg taaagattag cgtgagcttt accgagagct gcaggagtaa ggacaggaag   1020
gtgctgtaca caggagcaga gcgcgacgtg cgggcggagt gcggtctgct ccttagccct   1080
gtcagtgggg acgtgcatgc ttgtcccttt ggcgggagtg ttggtgacgg ggtaggcata   1140
gggggtgaga gtgctgataa gaaggatgag gagaatgagc tggatcagga aaagagagtg   1200
gagtatgcag tgctcgatga gttagaagat tttactgaca atttggagct agatgaagaa   1260
ggagcaggcg ggttcacggc taaagcaatc gttcagagag acagagtgga tgaagaggcc   1320
ttgaatttcc cctacgagga tgactttgac aacgatgtgg atgctctgct ggaagaaggc   1380
ctttgtgccc ccaaaaagag gcgaacagag gaaaaatatg gcggagacag cgaccatccg   1440
tccgatggag agacaagtgt gcagccgatg atgaccaaga ttaaaacagt gctcaaaagt   1500
cgtggccgcc cacctacaga gccgctgccc gacgggtgga tcatgacatt ccataactct   1560
ggagtcccgg tgtacctaca cagagagtct cgggtggtca cctggtccag gccatacttc   1620
ttgggaacgg gaagcatacg gaaacacgac cctcctctga gtagcatccc ttgtctgcat   1680
tataagaaaa tgaaggacaa cgaggaacgg gagcaaagca gtgacctcac ccctagtggg   1740
gatgtgtccc ccgtcaagcc cctgagccga tctgcagagc tggagtttcc cctggatgag   1800
cctgactcta tgggtgctga cccggggccc ccggacgaga aagacccact aggggctgag   1860
gcagcccctg gggccctggg gcaggtgaag gccaaagtcg aggtgtgcaa agatgaatcc   1920
```

```
gttgatctcg aggaatttcg aagctacctg gagaagcgtt ttgactttga gcaagttact   1980
gtgaaaaaat tcaggacttg ggctgagcgg cggcaattca atcgggaaat gaagcggaag   2040
caggcggagt ccgagaggcc catcttgcca gccaatcaga agctcattac tttatcagtg   2100
caagatgcac ccacaaagaa agagtttgtt attaacccca acgggaaatc cgaggtctgc   2160
atcctgcacg agtacatgca gcgtgtcctc aaggtccgcc ctgtctataa tttctttgaa   2220
tgtgagaacc caagtgagcc ttttggtgcc tcggtgacca ttgatggtgt gacttacgga   2280
tctggaactg caagcagcaa aaaacttgcg aagaataaag ctgcccgagc tacactggaa   2340
atcctcatcc ctgactttgt taaacagacc tctgaagaga gcccaaaga cagtgaagaa   2400 ctcgagtatt ttaaccacat cagcatcgag gactcgcggg tctacgagct gaccagcaag   2460
gctgggctgt tgtctccata tcagatcctc cacgagtgcc ttaaaagaaa ccatgggatg   2520
ggtgacacgt ctatcaagtt tgaagtggtt cctgggaaaa accagaagag tgaatacgtc   2580
atggcgtgtg gcaagcacac agtgcgcggg tggtgtaaga acaagagagt tggaaagcag   2640
ttagcctcac agaagatcct tcagctgctg cacccacatg tcaagaactg ggggtcttta   2700
ctgcgcatgt atggccgtga gagcagcaag atggtcaagc aggagacatc ggacaagagt   2760
gtgattgagc tgcagcagta tgccaagaag aacaagccca acctgcacat cctcagcaag   2820
ctccaagagg agatgaagag gctagctgag gaaagggagg agactcgaaa gaagcccaag   2880
atgtccattg tggcgtccgc ccagcctggc ggtgagcccc tgtgcaccgt ggacgtgtga   2940
gggaggtggc acgggccagg gcgcgggggc cgccagccgc acttctgagg agaccagcag   3000
tcatgcatcg tgcaccacag tgtcaggcct ccaacccacg ctccttccct gtggccaacc   3060
tgtgggcccg gccttagggt ggaggcttta gtgtacaggg acagccatgg ccacacagca   3120
cacatgtgga gcagcggctc tccctggaaa gctccaggcc tgaatggatg gactcagcga   3180
ctgcaccagt ggcagctggt gactgtggac agtggtggac cctgcttctg tgcacctgct   3240
gcaggctctt tttatgaagg cttttcatgaa ttttagtatg taatacgcac tgacgacaca   3300
tgatgcttgg atgacagatg agaggggatg gctgagtcct gtggctggcc cgtgatgcca   3360
ggtggcccat gtgcccaggg cgcctgcagg gctgctacag ggacctggtc aggaggtgca   3420
catggtgccc tgccctcacc caccctctgt gttttcccctt ctttgaaaag gtagaagaga   3480
aaggaatatt ttaaaccttt ttggcttaaa cagaatttta gcatcagaac tagctttctg   3540
ggattggagg caaaccatca aggtggtccc tctccagtct ggacacgatg ccagcaagga   3600
tgacgtcctg ccacctcctg gagttaccct ggcctcctag ggtcccttttt tctgatgaag   3660 tcttaattcc ctaaaagcgc ctctttggac actgaggccc tctctgcctt tcctggcctc   3720
cggcaacagt ttttacaaa gattttttgc agtcgagtcc atatgtccac ccattgattt   3780
ttaaagcttt tgtgatattt tagcattttg aaagactttc acagtgagag tagaaggtag   3840
atttggaatc atgcattta gcaagtggac ttgttgaaac aggaagcaag ggccttcagt   3900
gtagcccatt cttgatccag agctgttgcc tgtgacagcg gtttctctgg atgtcaaagg   3960
cagctgcctg gtgcccagct tgcttctcga ctggtggccc ctatgggtgg gtgtgcgatg   4020
gaaatgtgtt cctgccggag tctgaggcac cagggtgtgc tcaaaggctg ccctggtgg   4080 tggactggca cctgtgcaga gtgccgtgtg cttgtggtgc gccatctgaa gcaagagtcc   4140
agcgttctgc cgtgtctgtc ccccaccatg cccctacag gcggtactga tggcgctttt   4200
tttttttttt ctgtcaggaa aacaatgttg gcctgtgggc cgcccacaac atatccttcc   4260
```

-continued

| | |
|---|---|
| ctcactacct gtgtgaccaa ggttggcttc tgttgacctt taaaaaagaa accctcaact | 4320 |
| caaattgcta taattagaca cttgcttctg tcttgcctcc tgtctgcagc tgtgaatagt | 4380 |
| catttgactg tgactgttgc ccttagccag ccagatgcgc ctgtgaacca agcttcgtg | 4440 |
| cacatgtgtt cccctaaagg ttggggagcc tcgctgtgtc ttgctgttcc caggcaccac | 4500 |
| cacagcaggt gctgccatac tcttgtggtc tctgtgcgcc ccccccccc ccccacccgt | 4560 |
| ctgccaagca tgggtatgaa tcgtgcacac agccatgctt caaggccggg cagggggagc | 4620 |
| ctgtgctgat gccatccagg gcactgggct gtgcctggaa ggcgagcctt gattgtctga | 4680 |
| acacataaag caaactgtcc agaagggaaa aaaaaaaaa aaaaa | 4725 |

<210> SEQ ID NO 12
<211> LENGTH: 2505
<212> TYPE: DNA
<213> ORGANISM: Artificial Sequence
<220> FEATURE:
<223> OTHER INFORMATION: 3xFLAG-2xStrep-DGCR8 coding region

<400> SEQUENCE: 12

| | |
|---|---|
| atgggatccg ccggcgacta caaggaccac gacggcgatt ataaggatca cgacatcgac | 60 |
| tacaaagacg acgatgacaa gggcgccagc agcgcctggt cccaccctca gtttgagaag | 120 |
| ggcggaggct ctggcggcgg aagcggagga tctgcttgga gccaccccca gttcgaaaag | 180 |
| ggcgccgaga cagatgagag ccccctctcc gctcccgtgt ggcccgcagg agaagcggtg | 240 |
| atggagagcc gagctcgccc cttccaagcg ctgccccgtg agcagtctcc accacctccc | 300 |
| ctgcaaacgt ccagtggtgc agaggtaatg acgttggct ctggtggtga tggacagtcc | 360 |
| gaactccctg ctgaggaccc cttcaacttc tacggagctt ctcttctctc caaggatcc | 420 |
| ttctctaagg gccgcctcct catagacccg aactgtagtg gccacagccc gcgcaccgcc | 480 |
| cggcacgcac ctgcggtccg gaagttctcc cctgacctta gttgcttaa ggatgtaaag | 540 |
| attagcgtga gctttaccga gagctgcagg agtaaggaca ggaaggtgct gtacacagga | 600 |
| gcagagcgcg acgtgcgggc ggagtgcggt ctgctcctta gccctgtcag tggggacgtg | 660 |
| catgcttgtc cctttggcgg gagtgttggt gacggggtag gcataggggg tgagagtgct | 720 |
| gataagaagg atgaggagaa tgagctggat caggaaaaga gagtggagta tgcagtgctc | 780 |
| gatgagttag aagattttac tgacaatttg gagctagatg aagaaggagc aggcgggttc | 840 |
| acggctaaag caatcgttca gagagacaga gtggatgaag aggccttgaa tttcccctac | 900 |
| gaggatgact ttgacaacga tgtggatgct ctgctggaag aaggcctttg tgccccaaa | 960 |
| aagaggcgaa cagaggaaaa atatggcgga gacagcgacc atccgtccga tggagagaca | 1020 |
| agtgtgcagc cgatgatgac caagattaaa acagtgctca aaagtcgtgg ccgcccacct | 1080 |
| acagagccgc tgcccgacgg gtggatcatg acattccata actctggagt cccggtgtac | 1140 |
| ctacacagag agtctcgggt ggtcacctgg tccaggccat acttcttggg aacgggaagc | 1200 |
| atacggaaac acgaccctcc tctgagtagc atcccttgtc tgcattataa gaaaatgaag | 1260 |
| gacaacgagg aacgggagca agcagtgac ctcaccccta gtggggatgt gtcccccgtc | 1320 |
| aagcccctga ccgatctgc agagctggag tttcccctgg atgagcctga ctctatgggt | 1380 |
| gctgacccgg ggccccgga cgagaaagac ccactagggg ctgaggcagc ccctggggcc | 1440 |
| ctggggcagg tgaaggccaa agtcgaggtg tgcaaagatg aatccgttga tctcgaggaa | 1500 |
| tttcgaagct acctggagaa gcgttttgac tttgagcaag ttactgtgaa aaaattcagg | 1560 |
| acttgggctg agcggcggca attcaatcgg gaaatgaagc ggaagcaggc ggagtccgag | 1620 |

```
aggcccatct tgccagccaa tcagaagctc attactttat cagtgcaaga tgcacccaca    1680
aagaaagagt ttgttattaa ccccaacggg aaatccgagg tctgcatcct gcacgagtac    1740
atgcagcgtg tcctcaaggt ccgccctgtc tataatttct ttgaatgtga aacccaagt     1800 gagccttttg gtgcctcggt gaccattgat ggtgtgactt acggatctgg aactgcaagc    1860
agcaaaaaac ttgcgaagaa taaagctgcc cgagctacac tggaaatcct catccctgac    1920
tttgttaaac agacctctga agagaagccc aaagacagtg aagaactcga gtattttaac    1980
cacatcagca tcgaggactc gcgggtctac gagctgacca gcaaggctgg gctgttgtct    2040
ccatatcaga tcctccacga gtgccttaaa agaaaccatg ggatgggtga cacgtctatc    2100
aagtttgaag tggttcctgg gaaaaaccag aagagtgaat acgtcatggc gtgtggcaag    2160
cacacagtgc gcgggtggtg taagaacaag agagttggaa agcagttagc ctcacagaag    2220
atccttcagc tgctgcaccc acatgtcaag aactgggggt ctttactgcg catgtatggc    2280
cgtgagagca gcaagatggt caagcaggag acatcggaca agagtgtgat tgagctgcag    2340
cagtatgcca agaagaacaa gcccaacctg cacatcctca gcaagctcca agaggagatg    2400
aagaggctag ctgaggaaag ggaggagact cgaaagaagc ccaagatgtc cattgtggcg    2460
tccgcccagc ctggcggtga gcccctgtgc accgtggacg tgtga                   2505
```

```
<210> SEQ ID NO 13
<211> LENGTH: 183
<212> TYPE: DNA
<213> ORGANISM: Artificial Sequence
<220> FEATURE:
<223> OTHER INFORMATION: 3xFLAG-2xStrep-DGCR8 insertion sequence

<400> SEQUENCE: 13
ggatccgccg gcgactacaa ggaccacgac ggcgattata aggatcacga catcgactac     60
aaagacgacg atgacaaggg cgccagcagc gcctggtccc accctcagtt tgagaagggc    120
ggaggctctg gcgcggaag cggaggatct gcttggagcc accccagtt cgaaaagggc      180 gcc                                                                  183
```

```
<210> SEQ ID NO 14
<211> LENGTH: 25
<212> TYPE: DNA
<213> ORGANISM: Artificial Sequence
<220> FEATURE:
<223> OTHER INFORMATION: DROSHA_sgRNA-upper

<400> SEQUENCE: 14
caccgtaaag gagggcatgc aagtg                                           25
```

```
<210> SEQ ID NO 15
<211> LENGTH: 25
<212> TYPE: DNA
<213> ORGANISM: Artificial Sequence
<220> FEATURE:
<223> OTHER INFORMATION: DROSHA_sgRNA-lower

<400> SEQUENCE: 15
aaaccacttg catgccctcc tttac                                           25
```

```
<210> SEQ ID NO 16
<211> LENGTH: 25
<212> TYPE: RNA
<213> ORGANISM: Artificial Sequence
<220> FEATURE:
```

<223> OTHER INFORMATION: DGCR8_sgRNA-upper

<400> SEQUENCE: 16
caccggccca cacgggagcg gagag                                    25

<210> SEQ ID NO 17
<211> LENGTH: 25
<212> TYPE: DNA
<213> ORGANISM: Artificial Sequence
<220> FEATURE:
<223> OTHER INFORMATION: DGCR8_sgRNA-lower

<400> SEQUENCE: 17
aaacctctcc gctcccgtgt gggcc                                    25

<210> SEQ ID NO 18
<211> LENGTH: 4101
<212> TYPE: DNA
<213> ORGANISM: Artificial Sequence
<220> FEATURE:
<223> OTHER INFORMATION: SpCas9

<400> SEQUENCE: 18
gacaagaagt acagcatcgg cctggacatc ggcaccaact ctgtgggctg ggccgtgatc        60
accgacgagt acaaggtgcc cagcaagaaa ttcaaggtgc tgggcaacac cgaccggcac      120
agcatcaaga gaaacctgat cggagccctg ctgttcgaca gcggcgaaac agccgaggcc      180
acccggctga agaaccgc cagaagaaga tacaccagac ggaagaaccg gatctgctat        240
ctgcaagaga tcttcagcaa cgagatggcc aaggtggacg acagcttctt ccacagactg      300
gaagagtcct tcctggtgga agaggataag aagcacgagc ggcaccccat cttcggcaac      360
atcgtggacg aggtggccta ccacgagaag taccccacca tctaccacct gagaaagaaa      420
ctggtggaca gcaccgacaa ggccgacctg cggctgatct atctggccct ggcccacatg      480
atcaagttcc ggggccactt cctgatcgag ggcgacctga accccgacaa cagcgacgtg      540
gacaagctgt tcatccagct ggtgcagacc tacaaccagc tgttcgagga aaaccccatc      600
aacgccagcg gcgtggacgc caaggccatc ctgtctgcca gactgagcaa gagcagacgg      660
ctggaaaatc tgatcgccca gctgcccggc gagaagaaga atggcctgtt cggaaacctg      720
attgccctga gcctgggcct gacccccaac ttcaagagca acttcgacct ggccgaggat      780
gccaaactgc agctgagcaa ggacacctac gacgacgacc tggacaacct gctggcccag      840
atcggcgacc agtacgccga cctgtttctg gccgccaaga acctgtccga cgccatcctg      900
ctgagcgaca tcctgagagt gaacaccgag atcaccaagg cccccctgag cgcctctatg      960
atcaagagat acgacgagca ccaccaggac ctgaccctgc tgaaagctct cgtgcggcag     1020
cagctgcctg agaagtacaa agagattttc ttcgaccaga gcaagaacgg ctacgccggc     1080
tacattgacg gcggagccag ccaggaagag ttctacaagt tcatcaagcc catcctggaa     1140
aagatggacg gcaccgagga actgctcgtg aagctgaaca gagaggacct gctgcggaag     1200
cagcggacct tcgacaacgg cagcatcccc caccagatcc acctgggaga gctgcacgcc     1260
attctgcggc ggcaggaaga tttttaccca ttcctgaagg acaaccggga aaagatcgag     1320
aagatcctga ccttccgcat cccctactac gtgggccctc tggccagggg aaacagcaga     1380
ttcgcctgga tgaccagaaa gagcgaggaa accatcaccc cctggaactt cgaggaagtg     1440
gtggacaagg gcgcttccgc ccagagcttc atcgagcgga tgaccaactt cgataagaac     1500
ctgcccaacg agaaggtgct gcccaagcac agcctgctgt acgagtactt caccgtgtat     1560

```
aacgagctga ccaaagtgaa atacgtgacc gagggaatga gaaagcccgc cttcctgagc    1620
ggcgagcaga aaaaggccat cgtggacctg ctgttcaaga ccaaccggaa agtgaccgtg    1680
aagcagctga agaggactac cttcaagaaa atcgagtgct tcgactccgt ggaaatctcc    1740
ggcgtggaag atcggttcaa cgcctccctg ggcacatacc acgatctgct gaaaattatc    1800
aaggacaagg acttcctgga caatgaggaa aacgaggaca ttctggaaga tatcgtgctg    1860
accctgacac tgtttgagga cagagagatg atcgaggaac ggctgaaaac ctatgcccac    1920
ctgttcgacg acaaagtgat gaagcagctg aagcggcgga gatacaccgg ctggggcagg    1980
ctgagccgga agctgatcaa cggcatccgg gacaagcagt ccggcaagac aatcctggat    2040
ttcctgaagt ccgacggctt cgccaacaga aacttcatgc agctgatcca cgacgacagc    2100 ctgacctttta aagaggacat ccagaaagcc caggtgtccg gccagggcga tagcctgcac    2160
gagcacattg ccaatctggc cggcagcccc gccattaaga agggcatcct gcagacagtg    2220
aaggtggtgg acgagctcgt gaaagtgatg ggccggcaca gcccgagaa catcgtgatc    2280 gaaatggcca gagagaacca gaccacccag aagggacaga gaacagccg cgagagaatg    2340 aagcggatcg aagagggcat caaagagctg ggcagccaga tcctgaaaga acaccccgtg    2400
gaaaacaccc agctgcagaa cgagaagctg tacctgtact acctgcagaa tgggcgggat    2460
atgtacgtgg accaggaact ggacatcaac cggctgtccg actacgatgt ggaccatatc    2520
gtgcctcaga gctttctgaa ggacgactcc atcgacaaca aggtgctgac cagaagcgac    2580
aagaaccggg gcaagagcga caacgtgccc tccgaagagg tcgtgaagaa gatgaagaac    2640
tactggcggc agctgctgaa cgccaagctg attacccaga gaaagttcga caatctgacc    2700
aaggccgaga gaggcggcct gagcgaactg gataaggccg gcttcatcaa gagacagctg    2760
gtggaaaccc ggcagatcac aaagcacgtg gcacagatcc tggactcccg gatgaacact    2820
aagtacgacg agaatgacaa gctgatccgg gaagtgaaag tgatcaccct gaagtccaag    2880
ctggtgtccg atttccggaa ggatttccag ttttacaaag tgcgcgagat caacaactac    2940
caccacgccc acgacgccta cctgaacgcc gtcgtgggaa ccgccctgat caaaaagtac    3000
cctaagctgg aaagcgagtt cgtgtacggc gactacaagg tgtacgacgt gcggaagatg    3060
atcgccaaga gcgagcagga aatcggcaag gctaccgcca agtacttctt ctacagcaac    3120
atcatgaact ttttcaagac cgagattacc ctggccaacg gcgagatccg gaagcggcct    3180
ctgatcgaga caaacggcga aaccggggag atcgtgtggg ataagggccg ggattttgcc    3240
accgtgcgga aagtgctgag catgccccaa gtgaatatcg tgaaaaagac cgaggtgcag    3300
acaggcggct tcagcaaaga gtctatcctg cccaagagga acagcgataa gctgatcgcc    3360
agaaagaagg actgggaccc taagaagtac ggcggcttcg acagcccac cgtggcctat    3420 tctgtgctgg tggtggccaa agtggaaaag ggcaagtcca gaaactgaa gagtgtgaaa    3480 gagctgctgg gatcaccat catggaaaga agcagcttcg agaagaatcc catcgacttt    3540
ctggaagcca agggctacaa agaagtgaaa aaggacctga tcatcaagct gcctaagtac    3600
tccctgttcg agctggaaaa cggcggaag agaatgctgg cctctgccgg cgaactgcag    3660
aagggaaacg aactggccct gccctccaaa tatgtgaact tcctgtacct ggccagccac    3720
tatgagaagc tgaagggctc ccccgaggat aatgagcaga acagctgtt tgtggaacag    3780 cacaagcact acctggacga gatcatcgag cagatcagcg agttctccaa gagagtgatc    3840
ctggccgacg ctaatctgga caaagtgctg tccgcctaca acaagcaccg ggataagccc    3900
```

-continued

```
atcagagagc aggccgagaa tatcatccac ctgtttaccc tgaccaatct gggagcccct    3960
gccgccttca agtactttga caccaccatc gaccggaaga ggtacaccag caccaaagag    4020
gtgctggacg ccaccctgat ccaccagagc atcaccggcc tgtacgagac acggatcgac    4080
ctgtctcagc tgggaggcga c                                              4101

<210> SEQ ID NO 19
<211> LENGTH: 20
<212> TYPE: DNA
<213> ORGANISM: Artificial Sequence
<220> FEATURE:
<223> OTHER INFORMATION: DROSHA forward primer

<400> SEQUENCE: 19
catcagaagc ggttcatcga                                                  20

<210> SEQ ID NO 20
<211> LENGTH: 24
<212> TYPE: DNA
<213> ORGANISM: Artificial Sequence
<220> FEATURE:
<223> OTHER INFORMATION: DROSHA reverse primer

<400> SEQUENCE: 20
aagtaatgca cattcaccaa agtc                                             24

<210> SEQ ID NO 21
<211> LENGTH: 20
<212> TYPE: DNA
<213> ORGANISM: Artificial Sequence
<220> FEATURE:
<223> OTHER INFORMATION: DGCR8 forward primer

<400> SEQUENCE: 21
gactgtccat caccaccaga                                                  20

<210> SEQ ID NO 22
<211> LENGTH: 20
<212> TYPE: DNA
<213> ORGANISM: Artificial Sequence
<220> FEATURE:
<223> OTHER INFORMATION: DGCR8 reverse primer

<400> SEQUENCE: 22
caatgtggcc agcttgacta                                                  20
```